(12) United States Patent
Mesaros et al.

(10) Patent No.: US 6,475,228 B1
(45) Date of Patent: Nov. 5, 2002

(54) SYSTEM AND METHOD OF CONTROLLING PRESSURE IN A SURGICAL TOURNIQUET

(75) Inventors: Robert Mesaros, Bozeman, MT (US); Michael E. Hovanes, Redmond, WA (US); William Clem, Bozeman, MT (US); Cory Williamson, Bozeman, MT (US); Martin Albini, Bozeman, MT (US); Darius Eghbal, Bozeman, MT (US); Erik Green, Bozeman, MT (US); Jason Stewart, Bozeman, MT (US)

(73) Assignee: Instrumed, Inc., Woodinville, WA (US)

( * ) Notice: Subject to any disclaimer, the term of this patent is extended or adjusted under 35 U.S.C. 154(b) by 0 days.

(21) Appl. No.: 09/504,131

(22) Filed: Feb. 15, 2000

Related U.S. Application Data

(63) Continuation of application No. 09/280,312, filed on Mar. 29, 1999, now Pat. No. 6,051,016.

(51) Int. Cl.$^7$ .............................................. A61B 17/12
(52) U.S. Cl. ..................................................... 606/202
(58) Field of Search ................................ 606/202, 201, 606/203; 128/681, 327, 680, 686

(56) References Cited

U.S. PATENT DOCUMENTS

| | | | |
|---|---|---|---|
| 4,321,929 A | | 3/1982 | Lemelson et al. |
| 4,671,290 A | * | 6/1987 | Miller et al. ................ 128/681 |
| 4,869,265 A | | 9/1989 | McEwen |
| 5,307,791 A | * | 5/1994 | Senoue et al. ................ 601/9 |
| 5,366,474 A | * | 11/1994 | Blumenkanz et al. ....... 606/202 |
| 5,556,415 A | * | 9/1996 | Mc Ewen et al. .......... 606/202 |
| 5,911,735 A | | 6/1999 | McEwen et al. |

* cited by examiner

*Primary Examiner*—Kevin T. Truong
(74) *Attorney, Agent, or Firm*—Reed Smith LLP

(57) ABSTRACT

A system and method of controlling the pressure within a surgical tourniquet so as selectively to occlude blood flow within a portion of a limb of a patient, wherein the pressure within an inflatable cuff surrounding a portion of a limb of a patient is changed by automatically opening a first valve connected to a controller and located within a first conduit between an inflatable bladder and the inflatable cuff, when the pressure in the inflatable cuff is different from that in the inflatable bladder. In another aspect, a system and method of controlling the pressure within a surgical tourniquet so as selectively to occlude blood flow within a portion of a limb of a patient within five seconds. In another aspect, a system and method of detecting a leak in a surgical tourniquet. In another aspect, a surgical tourniquet that, from an inflated state, may enter a deflated state, a set state, a default display state, or an off state. In another aspect, a surgical tourniquet mounted in a housing selectively closed around a pole, wherein the center of gravity of the housing is located within the pole. In another aspect, a surgical tourniquet controlled by means of a graphical user interface. In another aspect, a method of detecting a stuck solenoid valve in a surgical tourniquet.

21 Claims, 19 Drawing Sheets

| Label | Symbol | Number |
|---|---|---|
| ALARM EMERGENCY |  | 602 |
| ALARM SOUND OFF |  | 604 |
| AIR LEAK |  | 606 |
| BATTERY CHARGING |  | 608 |
| BATTERY |  | 610 |
| CAUTION |  | 612 |
| CUFF PRESSURIZED |  | 614 |
| DECREASE | — | 616 |
| DEFLATED |  | 618 |
| INFLATE |  | 620 |
| INCREASE |  | 622 |
| ON/OFF |  | 624 |
| PRINTER |  | 626 |
| READY |  | 628 |
| DEFAULT DISPLAY |  | 630 |
| SERVICE |  | 632 |
| SET/SAVE |  | 634 |
| TESTING |  | 636 |
| TIME COUNT DOWN |  | 638 |
| TIME COUNT UP |  | 640 |

SYSTEM AND METHOD OF CONTROLLING PRESSURE IN A SURGICAL TOURNIQUET

The present application is a continuation of application Ser. No. 09/280,312, file date Mar. 29, 1999 now U.S. Pat. No. 6,051,016.

FIELD OF THE INVENTION

The present invention relates generally to surgical tourniquets. More particularly, the present invention relates to various aspects of a system and method for controlling pressure in a surgical tourniquet.

BACKGROUND

Surgical tourniquets are widely used during surgical procedures to occlude the flow of blood in a portion of a limb during the procedure, particularly in connection with arthroscopic procedures relating to the hand, wrist, elbow, foot, and knee, in which the existence of a bloodless field in the appropriate portion of a patient's limb may be required. Surgical tourniquets are similarly useful in other procedures in which the creation of a bloodless field is desirable, including nerve grafting and harvesting. It is particularly important in certain procedures that a surgeon be able to shut off the flow of blood extremely quickly during the procedure. Yet prior art surgical tourniquets typically require seven seconds or more for inflation before blood flow may be occluded. It is equally important that pressure be evenly maintained by a surgical tourniquet despite the manipulation by a surgeon of the limb in which blood flow is being occluded by the tourniquet, which manipulation tends to affect the pressure within the tourniquet. It is also important that the surgical tourniquet be easy to use and physically stable so that the surgeon may focus his attention on other aspects of the surgery.

It is therefore an object of the present invention to provide a dual reservoir equilibrium surgical tourniquet allowing swift inflation and deflation.

It is a further object of the present invention to provide a surgical tourniquet that can be inflated in less than five seconds.

It is a still further object of the present invention to provide a method for detecting air leaks in a surgical tourniquet.

It is a still further object of the present invention to provide a surgical tourniquet that from an inflated state may be deflated, reset to default values, adjusted to new values, or turned off.

It is a still further object of the present invention to provide a surgical tourniquet with a housing fitting around a pole and with a center of gravity within the pole.

It is a still further object of the present invention to provide a surgical tourniquet with an easy to use graphical user interface.

It is a still further object of the present invention to provide a method for detecting stuck valves in a surgical tourniquet.

SUMMARY OF THE INVENTION

The present invention is directed to a system and method of controlling the pressure within a surgical tourniquet so as selectively to occlude blood flow within a portion of a limb of a patient. The pressure within an inflatable cuff surrounding a portion of a limb of a patient is decreased by automatically opening a first valve connected to a controller and located within a first conduit between an inflatable bladder and the inflatable cuff, when the pressure in the inflatable cuff is greater than that in the inflatable bladder. The pressure within an inflatable cuff surrounding a portion of a limb of a patient is increased by automatically opening a first valve connected to a controller and located within a first conduit between an inflatable bladder and the inflatable cuff, when the pressure in the inflatable cuff is less than that in the inflatable bladder.

In another aspect, the present invention is directed to a system and method of controlling the pressure within a surgical tourniquet so as selectively to occlude blood flow within a portion of a limb of a patient, wherein the pressure within an inflatable cuff surrounding a portion of a limb of a patient is automatically altered by opening a first valve connected to a controller and located within a first conduit between an inflatable bladder and the inflatable cuff, and wherein the pressure within the inflatable cuff may be increased by a pump from a pressure equal to that of the surrounding atmosphere to a pressure sufficient to occlude the flow of blood in a portion of the patient's limb within five seconds.

In another aspect, the present invention is directed to a system and method of detecting a leak in a surgical tourniquet, including an inflatable cuff, wherein the pressure of gas within the inflatable cuff is increased until a target pressure is reached. The pressure of gas contained within the inflatable cuff is then repeatedly measured with a pressure sensor coupled to the inflatable cuff and connected to a controller. Data relating to each extraneous change in pressure are stored in a memory. All extraneous changes in pressure are then compared using predetermined criteria to determine if a leak has occurred.

In another aspect, the present invention is directed to a surgical tourniquet, including an inflatable cuff, containing a quantity of gas, and a controller, wherein from an inflated state the surgical tourniquet may enter a deflated state, a set state, a default display state, or an off state.

In another aspect, the present invention is directed to a surgical tourniquet, including an inflatable cuff, a controller connected to the inflatable cuff, and an electronic display connected to the controller and mounted in a housing selectively closed around a pole, wherein the center of gravity of the housing is located within the pole.

In another aspect the present invention is directed to a surgical tourniquet, including an inflatable cuff, a controller connected to the inflatable cuff, and a display connected to the controller, wherein a user controls the surgical tourniquet by means of a graphical user interface displayed on said display.

In another aspect, the present invention is directed to a method of detecting a stuck solenoid valve in a surgical tourniquet, wherein the current, if any, flowing through the solenoid valve is sensed. It is determined whether the solenoid valve is open based on the amount of current flowing through the solenoid valve. Whether the solenoid valve should be open is determined based on the current state of the surgical tourniquet. Whether the solenoid valve is stuck is then determined based on a comparison of whether the solenoid valve is open and whether it should be open, and, if the solenoid valve is stuck, any short circuited output is turned off.

In accordance with a further aspect, the present invention is directed to a method for controlling the operation of a surgical tourniquet. An input setting is received from a user through a graphical user-interface, wherein the input setting corresponds to a user-selected target pressure to be maintained in the surgical tourniquet during a medical procedure. The user-selected target pressure is compared, with a controller coupled to the user-interface, to a range of acceptable target pressures. If the user-selected target pressure is outside of the range of acceptable target pressures, the user-selected target pressure is rejected by the system. Alternatively, if the user-selected target pressure is within the range of acceptable target pressures, the surgical tourniquet is pressurized in accordance with the user-selected target pressure.

In accordance with a still further aspect, the present invention is directed to a further method for controlling the operation of a surgical tourniquet. In this further method, an input setting is received from a user through a graphical user-interface, wherein the input setting corresponds to a user-selected time period during which a target pressure is to be maintained in the surgical tourniquet during a medical procedure. The user-selected time period is compared, with a controller coupled to the user-interface, to a range of acceptable time periods. If the user-selected time period is outside of the range of acceptable time periods, the user-selected time period is rejected by the system. Alternatively, if the user-selected time period is within the range of acceptable time periods, a timer is set in the surgical tourniquet in accordance with the user-selected time period. An audible alarm is then sounded upon expiration of the user-selected time period. In a particularly preferred embodiment, a user can optionally delay deflation of the surgical tourniquet for successive predetermined periods of time following expiration of the user-selected period of time by entering delay commands through the graphical-user interface. Entry of each delay command serves to silence an alarm resulting from expiration of a previous time period and also serves to reset the timer for a further predetermined time period, after which the alarm sounds again. After a predetermined number of iterations of this process, the system does not accept further delay commands and the alarm remains in a continuous on state.

In accordance with yet a further aspect, the present invention is directed to a still further method for controlling the operation of a surgical tourniquet. An input command is received from a user through a graphical user-interface, wherein the input command corresponds to an instruction to deflate the surgical tourniquet. Shortly thereafter, the pressure in the surgical tourniquet is sensed and the sensed pressure is compared with a pressure corresponding to the surgical tourniquet in its deflated state. If the sensed pressure exceeds the pressure corresponding to the surgical tourniquet in its deflated state by more than a predetermined amount, then an alarm is sounded.

DETAILED DESCRIPTION OF THE INVENTION

Figure 1:
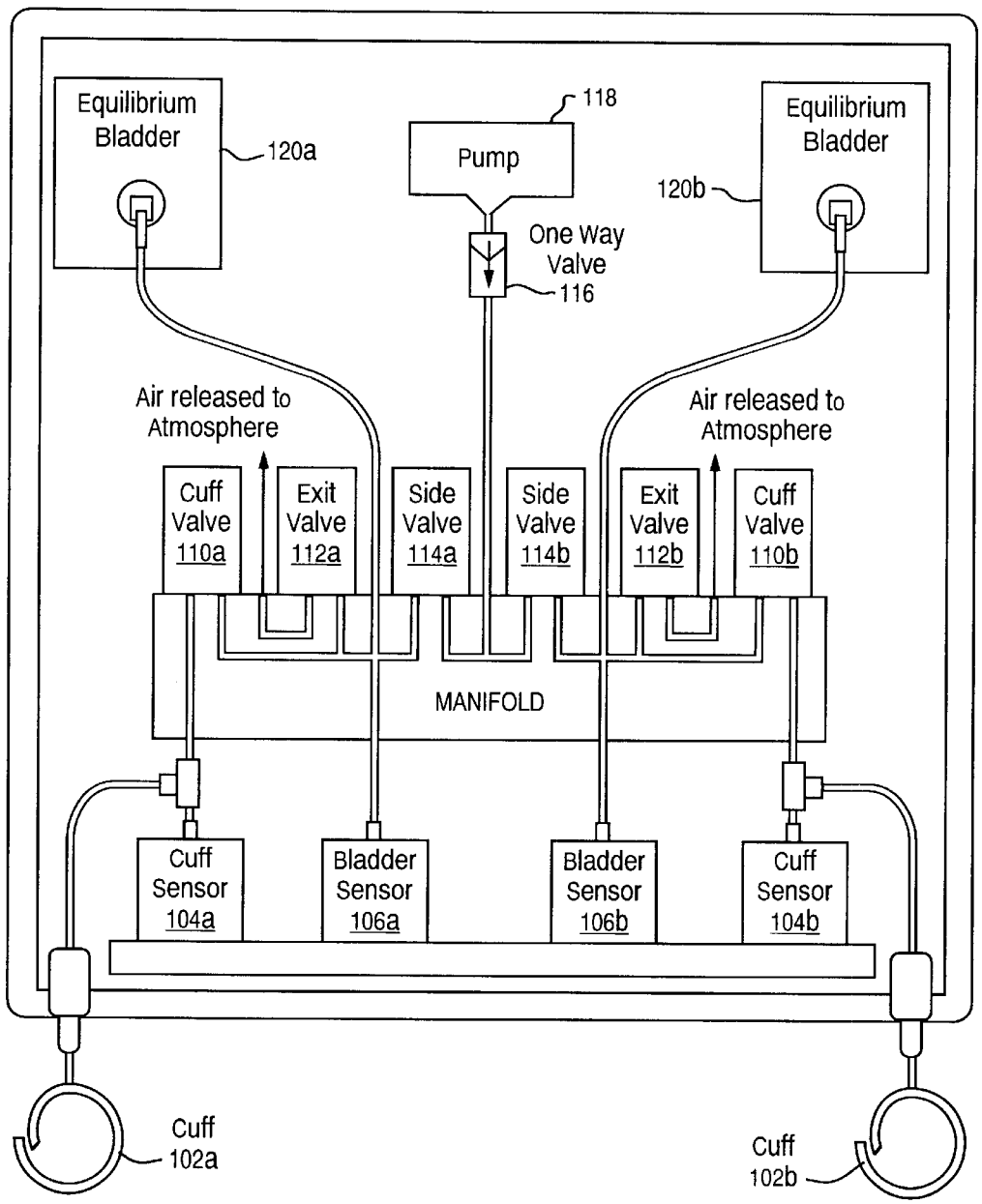
FIG. 1 is a block diagram illustrating the internal pneumatic system of a surgical tourniquet in accordance with a first preferred embodiment of the present invention.

The following definitions are provided to aid in construing the claims of the present application:

Default Display State. A state in which default values are displayed on a display. In certain embodiments, the inflatable cuff is deflated and subsequently re-inflated to a default pressure.

Deflated State. A state in which the pressure within the inflatable cuff does not exceed that of the surrounding atmosphere, but in which the surgical tourniquet has been in an inflated state since the last time in which it was in an off state.

Extraneous change in pressure. Any change in pressure within a reservoir that is not caused by the proper functioning of the valves and pump. Extraneous changes in pressure may be caused either by defects in the system, such as air leaks due to holes in reservoirs or air leaks due to valves failing to close completely (or at all), or by factors external to the system, such as movement of a patient's limb by a physician.

Gas. Any substance or collection of substances currently predominantly in a gaseous state. Gas is intended specifically to include ordinary air.

Inflated State. A state in which the pressure within the inflatable cuff exceeds that of the surrounding atmosphere.

Off State. A state in which the surgical tourniquet can be neither inflated nor deflated and in which no settings related to the surgical tourniquet may be altered. The off state is also characterized by a minimal consumption of electrical power.

Ready State. A state in which the surgical tourniquet has completed its system test and is ready for inflation, but in which the pressure within the inflatable cuff is still equal to that of the surrounding atmosphere and in which no inflation commands have yet been entered.

Reservoir. Any structure capable of containing gas, including such structures as an inflatable cuff and an inflatable bladder.

Selecting. The precise meaning of selecting a graphical user interface element depends on the input device and user interface being used. If the user is entering input with a touch screen, selecting an element typically means touching it. If the user is entering input with a mouse, selecting an element typically means clicking on it. If the user is entering input with a keyboard, selecting an element typically means pressing the appropriate key or keys.

Set State. A state in which commands relating to inflation of the surgical tourniquet may be entered. The inflatable cuff may be either inflated or deflated. In certain embodiments, the user interface will not accept potentially dangerous settings, such as a target pressure above 450 millimeters of mercury or a time period for occluding blood flow exceeding two hours.

Startup State. A state in which the surgical tourniquet runs various tests to ensure that it is working properly and in which the surgical tourniquet automatically fills its internal bladders to certain default pressures.

System Failure State. A state in which an error condition prevents the proper functioning of the system. Depending on the error condition encountered, the system may either enter an off state immediately or continue to function at least partially during the current operation before entering an off state.

Referring now to FIG. 1, the internal pneumatics of a preferred embodiment of the surgical tourniquet are illustrated. Two cuffs, 102A and 102B, are shown, as well as subsystems relating to each. In order to simplify the following discussion, only cuff 102A will be further described; however, the following description relates equally to cuff 102B and the system components relating to it. Moreover, although two cuffs are shown in FIG. 1, a surgical tourniquet in accordance with the present invention may have only one cuff, or may have more than two cuffs.

Cuff 102A is an inflatable device capable of being placed around a limb of a patient, much as a blood pressure cuff is placed around the arm of a patient whose blood pressure is being measured. It is connected by tubing, that runs partially within manifold 108 to valves 110A, 112A, 114A, and 116, sensors 104A and 106A, pump 118, and equilibrium bladder 120A. Pump 118 is used to pump gas into the system. Many gases may be used, but in the embodiment here illustrated, ordinary air from the surrounding atmosphere is used for reasons of cost and simplicity. The air is pumped through one way valve 116, which always allows air to be pumped into the system, but does not allow air to flow back to the pump. In other embodiments one way valve 116 may be a standard valve that must be opened and closed as appropriate, or may be omitted altogether. The use of a one way valve, however, prevents air from escaping from the system upon failure of side valve 114, permitting pressure to be maintained in the inflatable cuff until the completion of the current surgical procedure.

Opening side valve 114A allows air to be pumped through into equilibrium bladder 120A, while closing side valve 114A prevents air from flowing from the pump to equilibrium bladder 120A. In a single cuff system including a valve between the pump and the manifold, a side valve is not needed. However, in a multiple cuff system, the use of side valves allows the pressures in the several cuffs to be changed independently of each other by pumping air through one or more open side valves while one or more other side valves are closed. Side valve 114A is also connected by tubing to equilibrium bladder 120A, cuff valve 110A, exit valve 112A, and bladder sensor 106A. Thus any air pumped into the system through side valve 114A will always be able to flow freely to equilibrium bladder 120A and bladder sensor 106A. Moreover, air always flows freely between equilibrium bladder 120A and bladder sensor 106A, resulting in the pressures of equilibrium bladder 120A and bladder sensor 106A being equal, except possibly for minute periods of time when the system is not in an equilibrium state.

Cuff valve 110A, which is connected to tubing leading to cuff 102A and cuff sensor 104A from tubing leading to equilibrium bladder 120A, exit valve 112A, side valve 114A, and bladder sensor 106A, functions to separate cuff 102A and cuff sensor 104A from equilibrium bladder 120A and bladder sensor 106A, and to allow different pressures to be maintained in the cuff and bladder whenever the cuff valve is closed. Opening the cuff valve, on the other hand, will swiftly equalize the pressures in the cuff and equilibrium bladder. The free flow of air between cuff 102A and cuff sensor 104A allows the pressures at cuff 102A and cuff sensor 104A to be almost always almost precisely equal.

Opening exit valve 112A allows air to flow freely between equilibrium bladder 120A and the surrounding atmosphere, resulting in the pressure within the equilibrium bladder being reduced to that of the surrounding atmosphere almost immediately. Moreover, if cuff valve 110A and exit valve 112A are both open at once, air may flow freely between the surrounding atmosphere and the cuff as well, resulting in the pressure within the cuff being reduced to that of the surrounding atmosphere almost immediately.

Figure 2:
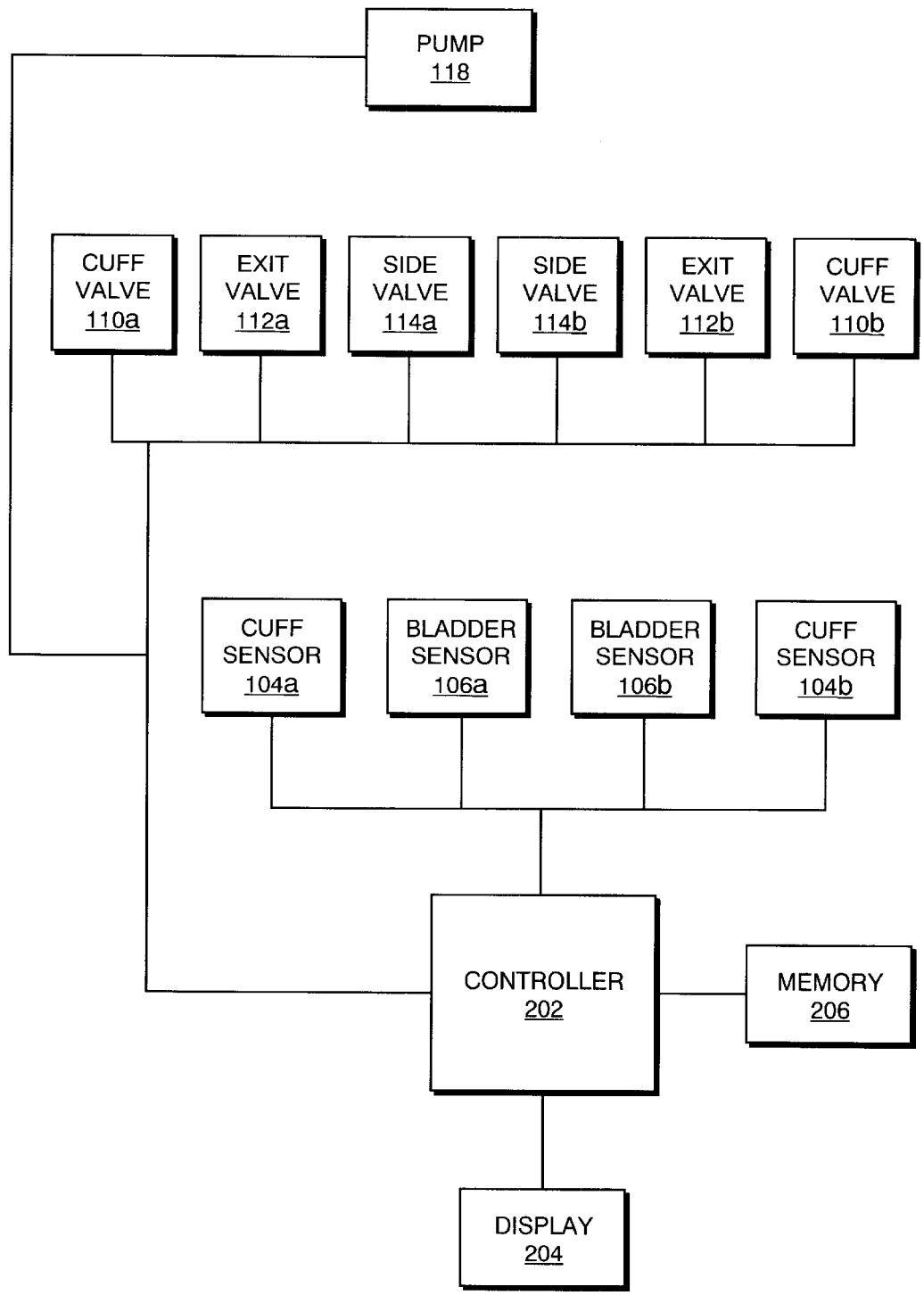
FIG. 2 is a block diagram illustrating a portion of the internal electronic system of a surgical tourniquet in accordance with a first preferred embodiment of the present invention.

Turning now to FIG. 2, a portion of the internal electronic system of a preferred embodiment of the present invention is illustrated. Controller 202, which includes a timer, is connected to display 204, memory 206, sensors 104A, 104B, 106A, and 106B, valves 110A, 110B, 112A, 112B, 114A, and 114B, and pump 118. The controller is able through software to turn on and off the pump as needed, to open and close the valves as needed, to monitor the sensors, to store data in the memory and to retrieve it as needed, and to communicate with the user via the display (which includes an input device in this embodiment).

Figure 3:
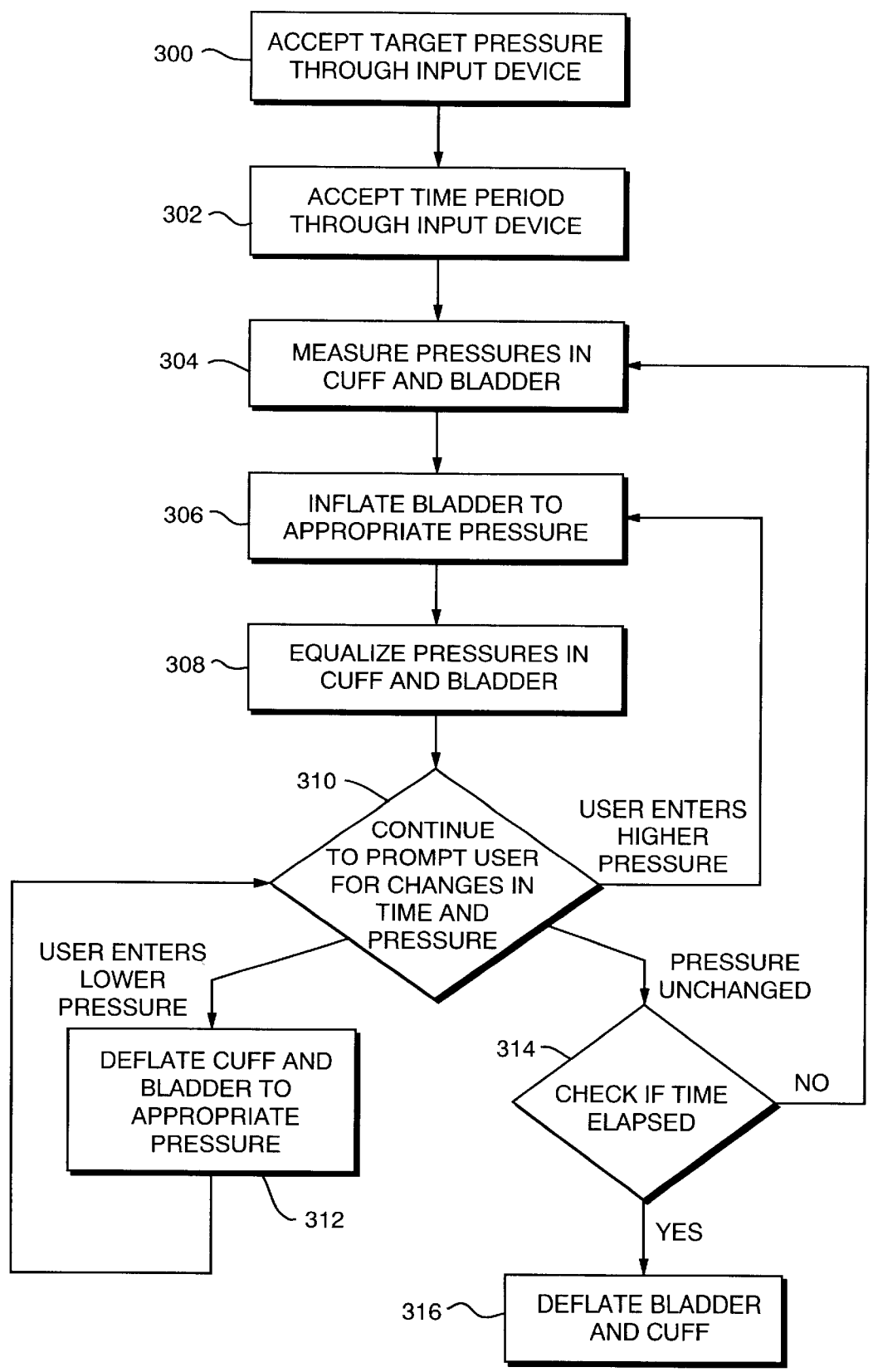
FIG. 3 is a flow diagram illustrating the operation of a surgical tourniquet in accordance with a first preferred embodiment of the present invention.

Referring to FIG. 3, a preferred embodiment of a method of controlling the pressure within a cuff of a surgical tourniquet is illustrated. This method is implemented in software on controller 202. In step 300, a target pressure is accepted from a user, as will be discussed below in connection with FIGS. 5A, 5B, and 6. Although the following description refers to only one cuff, it is to be understood that target pressures for multiple cuffs may be accepted in step 300 and each following step may be performed separately with regard to each cuff. A common target pressure is 300 millimeters of mercury, which is sufficient to occlude blood flow in a vein. In the preferred embodiments, the user interface will not accept a pressure exceeding 450 millimeters of mercury, which is generally considered to be unsafe. In step 302, a time period during which the target pressure is to be maintained is entered by the user through an input device, as is also discussed below in connection with FIGS. 5A, 5B, and 6. Normally, the time period will not exceed two hours, which is accepted as the maximum safe period during which blood flow may be occluded in a portion of a limb of a patient. In the preferred embodiments, the input device will not initially accept a time period exceeding two hours; however, the user may override the two hour limitation for an additional thirty minutes in five minute increments.

Although step 304 is depicted as occurring between steps 302 and 306, it in fact occurs repeatedly and continually throughout the process in the preferred embodiments. In step 304, controller 202 queries sensors 104 and 106 to determine the current pressures in the cuff and related equilibrium bladder.

In step 306, the equilibrium bladder is inflated to an appropriate pressure (or partially or entirely deflated if already inflated to an excessive pressure). This value depends on the target pressure, the current pressure in the cuff, and the relative volumes of the cuff and equilibrium bladder, including all related tubing (related tubing being tubing connected to the reservoir in question without being separated from it by a valve) and is given by the following equation in certain preferred embodiments:

$$P_B = P_T\left(1 + \frac{V_C}{V_B}\right) - P_C\left(\frac{V_C}{V_B}\right)$$

where $P_T$ is the target pressure for the cuff, $P_B$ is the pressure to which the bladder should be inflated, $P_C$ is the current pressure in the cuff, $V_B$ is the volume of the bladder including all related tubing, and $V_C$ is the volume of the cuff including all related tubing. As an example, if the user entered a target pressure of 300 millimeters of mercury in step 300, the cuff and equilibrium bladder were determined to both be filled with air at the pressure of 30 millimeters of mercury, and the volumes of the cuff and equilibrium bladder, including all related tubing, were equal, the equilibrium bladder would be inflated to a pressure of 570 millimeters of mercury.

In order to inflate the equilibrium bladder, the controller closes cuff valve 110 and exit valve 112, if open, and opens side valve 114, if closed. It then operates pump 118 and continuously monitors the pressure at bladder sensor 106 until the pressure measured by that sensor equals the appropriate pressure, which is 570 millimeters of mercury in the above example. At that point, the controller closes side valve 114 and ceases to operate pump 118.

The system could immediately proceed to execute step 308; however, in the preferred embodiment disclosed herein, the system waits between steps 306 and 308 until the user signals the system to proceed through the input device, as is discussed below in connection with FIGS. 5A, 5B, and 6. This allows a user to inflate the bladder ahead of time at any point during preparations for a surgical procedure and subsequently inflate the cuff almost instantaneously, that is to say in a small fraction of a second, at the appropriate point in the surgical procedure, so that blood flow is occluded for the minimum necessary interval of time.

In step 308, the system, either immediately or when ordered to, equalizes pressure between the equilibrium bladder and the cuff. The controller accomplishes this simply by opening cuff valve 110. At this point, the target pressure is achieved in the cuff, and the system can await further user input in step 310. In the preferred embodiment, however, the system continues to monitor and adjust the cuff pressure whenever the cuff is inflated. A small air leak may lead to a gradual loss of pressure. In addition, a surgeon's manipulation of a patient's limb may cause external pressure to be placed on the cuff or relieved, thereby altering the internal pressure of the cuff. In the preferred embodiment, the system continuously monitors such changes and adjusts the pressure of the cuff to maintain a pressure as close as possible to the target pressure and within predefined limits of the target pressure in much the same way as the system adjusts such pressure if the user alters the target pressure in step 310.

In an alternative embodiment, step 308 can be performed before step 306 is completed. For example, the cuff valve might be opened when the pressure within the equilibrium bladder had reached two-thirds of the pressure necessary to inflate the inflatable cuff to the target pressure. The pump would then continue to operate until both the equilibrium bladder and the inflatable cuff reached the target pressure. This embodiment offers greater assurance that the inflatable cuff will not be over-inflated and offers a degree of control over the speed of inflation.

If the user enters a higher desired pressure in step 310, the controller can simply open side valve 114 and operate pump 118 until the pressures measured at sensors 104 and 106 are equal to the target pressure. In the preferred embodiment, however, cuff valve 110 is closed before side valve 114 is opened, and the system returns to step 306, in order to allow a user to enter an altered target pressure before the moment at which the change is desired, allowing the system to achieve a new target pressure almost instantaneously when the desired moment of change arrives. Pump 118 is operated until an appropriate pressure is reached in the equilibrium bladder, as measured by the bladder sensor. The appropriate pressure is determined using the same equation as in step 306. To continue with the above example, if the user entered a target pressure of 320 millimeters of mercury, the equilibrium bladder would be inflated to a pressure of 340 millimeters of mercury. The controller then closes side valve 114 and opens cuff valve 110 in step 308, thereby equalizing pressures between the equilibrium bladder and the cuff and almost instantaneously achieving the target pressure.

Returning to step 310, if the user instead (or later) enters a lower target pressure, the system proceeds to step 312 in which the cuff and the equilibrium bladder are totally or partially deflated one or more times. In the preferred embodiment, the cuff valve is kept open while the exit valve is also opened to allow air to escape from both the cuff and the equilibrium bladder until the target pressure is measured at the cuff sensor, at which time the exit valve is closed. In other embodiments, however, the cuff valve might first be closed and the equilibrium bladder then partially or totally deflated prior to closure of the exit valve and equalization of pressures between the cuff and the equilibrium bladder through opening of the cuff valve. Doing so, however, requires multiple stages of deflation in certain instances in which relatively large declines in pressure are required, depending on the relative volumes and pressures of the cuff and equilibrium bladder. The system then returns to step 310.

Next, in step 314, the controller checks whether the time period entered in step 302 (which may have been modified in step 310) has expired. If this time period has expired, the system continues to step 316. If not, the system returns to step 304, so that the pressure within the cuff may be repeatedly measured, deviations from the target pressure may be corrected, and the user may be prompted for further input throughout the surgical procedure. Pressure readings in step 304 might be taken once per second in a preferred embodiment, but may be taken more or less frequently depending on system requirements and resources.

Finally, in step 316, when the time period entered in step 302 (which may have been modified in step 310) has expired, exit valve 112 is opened and the pressures within both the cuff and the equilibrium bladder are equalized with that of the surrounding atmosphere. In the preferred embodiments, however, the exit valve is not immediately opened at the end of the time period, but rather an alarm is sounded, which may be overridden by the user. If the user fails to override the alarm within a predetermined period of time, the exit valve is opened and the cuff is deflated. However, by overriding the alarm, the user can delay automatic deflation for additional periods of time. In no case, however, in the preferred embodiments, will the user be permitted to continuously occlude the flow of blood in a portion of a patient's limb for a period of time exceeding two hours and thirty minutes.

Figure 4:
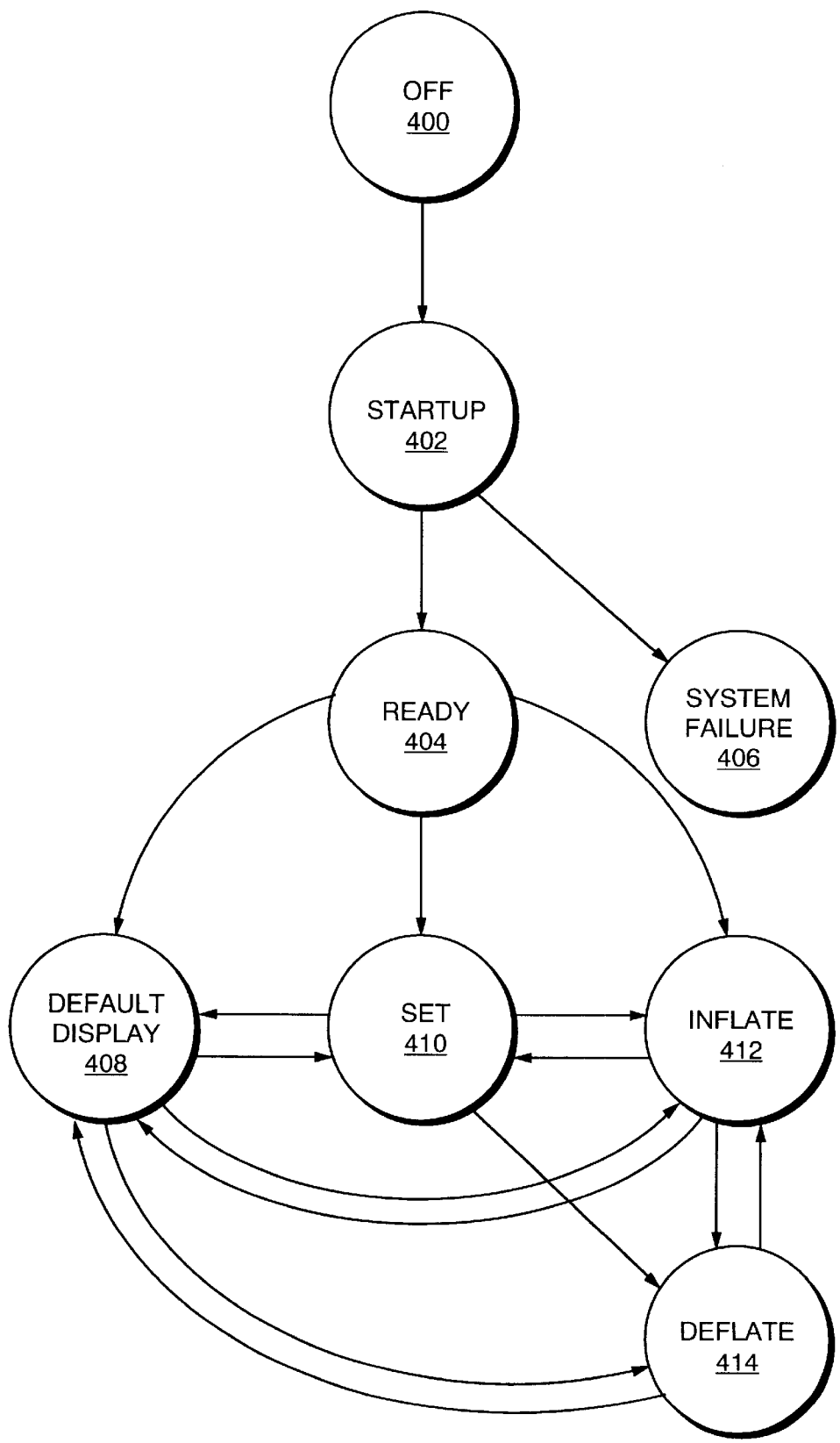
FIG. 4 is a state diagram illustrating the primary states of a surgical tourniquet in accordance with a first preferred embodiment of the present invention.

Referring to FIG. 4, the primary states in the preferred embodiment in which the system may be are illustrated. Initially, the system is in off state 400. From this state, the system may enter startup state 402. In the preferred embodiment disclosed herein, a user may cause the system to enter the startup state from the off state by pressing on/off button 524 illustrated in FIG. 5A. Although not shown in FIG. 4, a user may cause the system to reenter off state 400 from any other system state by pressing on/off button 524 at any time that the system is not in the off state.

While the system is in startup state 402, it executes a system test. If each component of the system test is satisfactorily completed, the system enters ready state 404; otherwise, it enters system failure state 406. During startup, the system will determine, inter alia, whether the current equilibrium bladders have been inflated an excessive number of times, rendering bladder failure likely, by monitoring a counter that is incremented every time the bladders are inflated. If the bladders have been inflated an excessive number of times, the system will enter the system failure state and a service icon will be illuminated. In addition, the system increments a counter each time it enters the startup state without subsequently entering the ready state. If the counter exceeds a predetermined limit (most likely due to software failure), the system will likewise enter the system failure and a service icon will be illuminated. From state 406, the system may be turned off and subsequently repaired. Although not shown, the system may enter the system failure state from any other state at any time upon the occurrence of any major component failure preventing the correct operation of the system.

From state 404, in addition to being able to enter states 400 and 406, as discussed above, the system may enter any of states 408, 410, or 412, depending on the actions of the user of the system. If the user presses default display button 522 in FIG. 5A, the system enters default display state 408 in which it displays the default time and pressure settings for the system, as originally set in the factory, or as since modified by a user. The system also deflates the cuffs and equilibrium bladders.

In set state 410, the user is able to set time and pressure settings for the cuffs for a surgical procedure, and also to set default values for those settings, as described below in connection with FIG. 5A. In inflate state 412, the system inflates the cuffs to the target pressures set in step 410 or the current default pressures previously displayed in step 404 or step 408 (or both), as may be applicable. In deflate state 414, the system deflates the cuffs and equilibrium bladders so that the pressures within such reservoirs are equal to that of the surrounding atmosphere, but the system does not alter the set times and pressures. Thus, the user may re-inflate each cuff with the touch of a button (518).

Figure 5A:
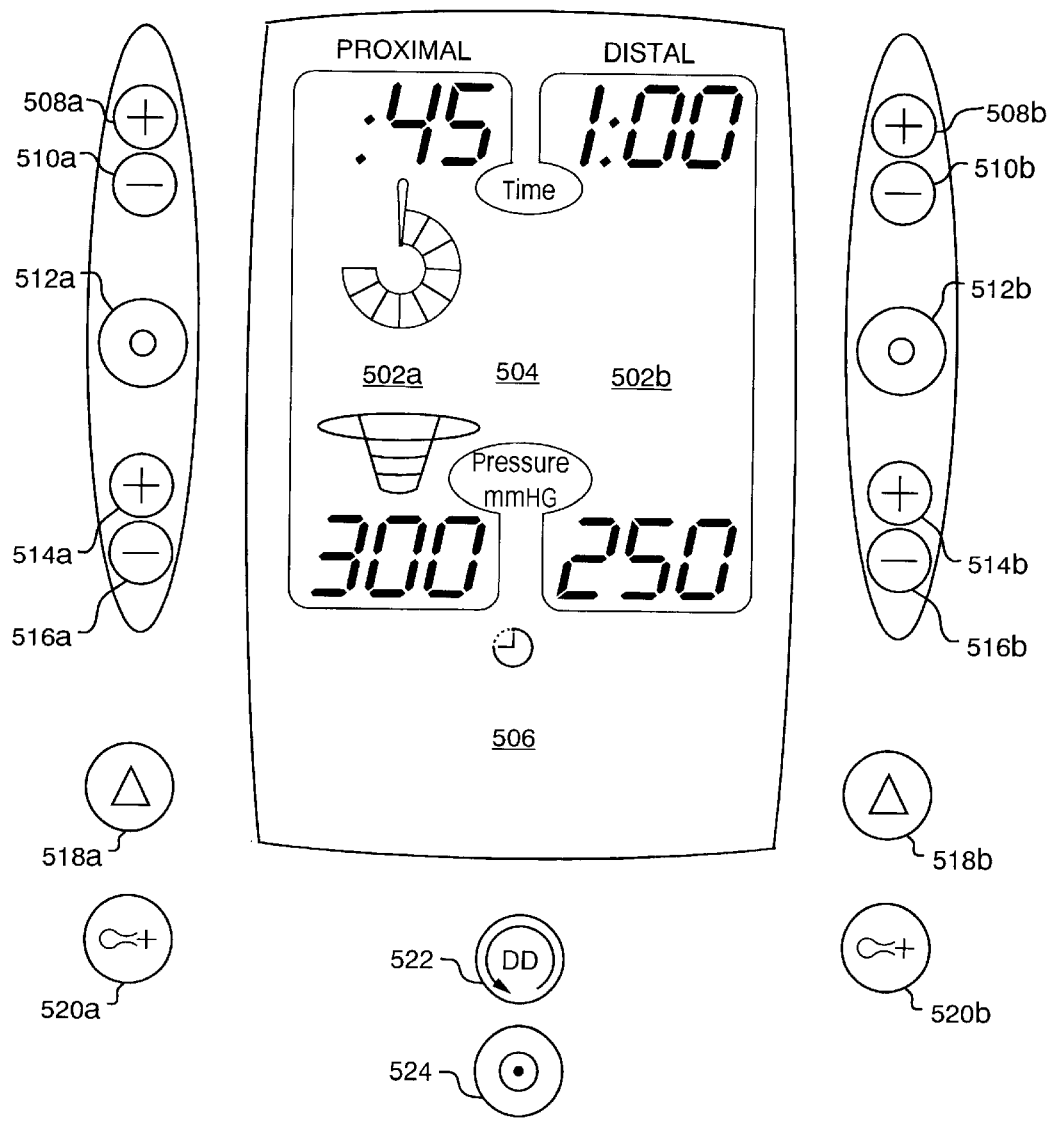
FIGS. 5A and 5B are block diagrams illustrating the appearance of user interface elements of a combined display and user input device of a surgical tourniquet in accordance with a first preferred embodiment of the present invention.

From any of default display state 408, set state 410, inflate state 412, or deflate state 414, the user may cause the system to enter any of default display state 408, set state 410, inflate state 412, or deflate state 414 by pressing the appropriate buttons, 522 in the case of default display state 408, any of 508, 510, 514, or 516 in the case of set state 410, 518 in the case of inflate state 412, or 520 in the case of deflate state 414, all as shown in FIG. 5A and described below. The user may also cause the system to enter the off state, as discussed above.

Referring now to FIG. 5A, an exemplary display incorporating a graphical user interface is shown. The display includes four areas for information to be displayed and several sets of buttons. Regions 502A and 502B display data relating to the proximal and distal cuffs respectively. Each of the two display areas is divided into an upper region in which data relating to the amount of time that the appropriate cuff will be pressurized is set forth and a lower region in which data relating to the pressure to be achieved in the appropriate cuff is displayed. The upper area can be configured to show either the amount of time during which the appropriate cuff has been inflated or the amount of time remaining until the cuff is deflated, in either case in both textual and graphical form. The temporal graphical element is in the form of two concentric segmented circles, with each segment of each circle representing a portion of an hour. As time elapses, segments are either illuminated or turned off, depending on the configuration. The lower area shows the current pressure when in an inflated state (or the pressure to be achieved in other states) in both textual and graphical form. As can be seen from FIG. 5B, the graphical pressure element is in the form of a rounded, inverted, segmented cone bisected by an ellipse. When the system is in an inflated state and the pressure in the cuff is equal to the target pressure, the ellipse and all segments below it are illuminated, as is shown in FIG. 5A. When the system is in an inflated state but the cuff pressure is below the target pressure, fewer segments are illuminated. When the system is in an inflated state but the cuff pressure is above the target pressure, more segments are illuminated. Thus, the user can determine at a glance whether the cuff is at the target pressure without the need for mental computations.

Region 504, which is located between regions 502A and 502B, and region 506, which is located below regions 502A, 502B, and 504, are used to display icons conveying information about the system to the user thereof. These icons are discussed below in connection with FIG. 6.

Buttons 508A, 510A, 512A, 514A, 516A, 518A, and 520A relate to the proximal cuff, while buttons 508B, 510B, 512B, 514B, 516B, 518B, and 520B relate to the distal cuff. Buttons 522 and 524 relate to both cuffs. Buttons 508A and 508B may be used while in a set state to increase the amount of time that a cuff will be inflated in five minute increments, while buttons 510A and 510B may be used to decrease the amount of time that a cuff will be inflated in five minute increments. Similarly, buttons 514A and 514B may be used while in a set state to increase the pressure of a cuff once it is inflated in five millimeter of mercury increments, while buttons 516A and 516B may be used while in a set state to decrease the pressure of a cuff once it is inflated in five millimeter of mercury increments. Buttons 512A and 512B may then be used to save the changed values, causing the cuff to be inflated or deflated, as discussed in connection with FIG. 3. The failure to press buttons 512A and 512B will result in changes to the settings relating to the corresponding cuffs being discarded upon the system's exit from the set state. The user will receive an audible caution in this case to indicate that the changes have been discarded. Settings may additionally be saved as default settings by holding down the appropriate inflate button, 518A or 518B, and then pressing the appropriate set button, 512A or 512B. A user may change the default settings from the factory set settings if the user commonly employs different pressure settings in surgical procedures. For example, a specialist in pediatric surgery would likely employ lower pressures than surgeons performing surgeries on adults.

Buttons 518A and 518B are used to inflate the respective cuffs using the last saved pressure and time duration values. Buttons 520A and 520B are correspondingly used to deflate the respective cuffs. Button 522 causes the system to enter the default display state and sets all values to the last saved default values (which, if the system is in the inflated state causes the cuff to be inflated to the default pressure), while button 524 toggles the system between on and off states.

Figure 5B:
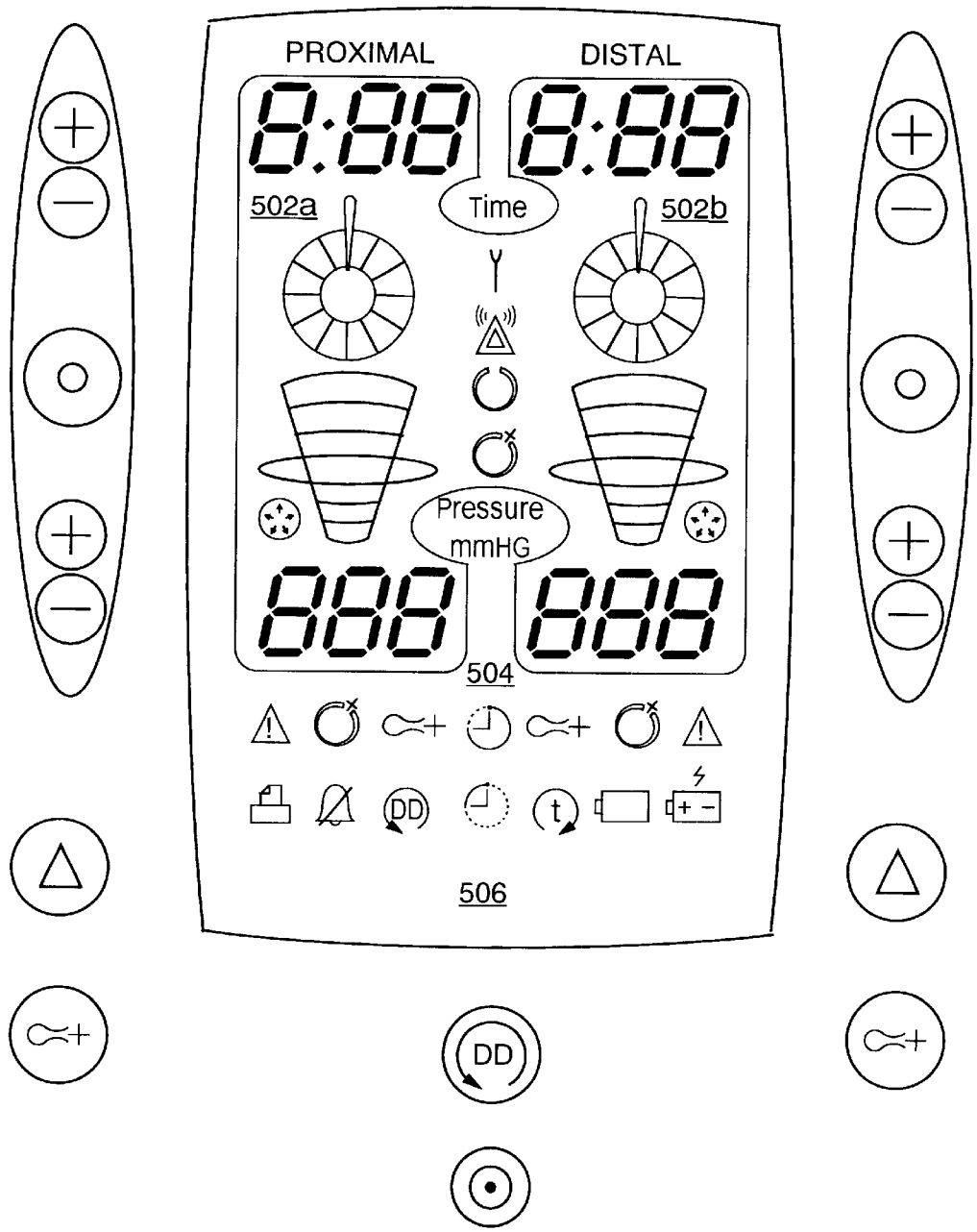

FIG. 5B shows the display with a maximum number of icons shown. Depending on the circumstances, icons may be shown in any or all of regions 502A, 502B, 504, or 506. An alarm icon (not shown) is also displayed on top of the system in green whenever the system is on and in red whenever an alarm condition is currently occurring.

Figure 6:
FIG. 6 illustrates symbols used in a user interface of a surgical tourniquet in accordance with a first preferred embodiment of the present invention.
Figure 6:
Figure 6:
Figure 6:
Figure 6:
Figure 6:
Figure 6:
Figure 6:
Figure 6:
Figure 6:
Figure 6:
Figure 6:
Figure 6:
Figure 6:
Figure 6:
Figure 6:
Figure 6:
Figure 6:
Figure 6:

FIG. 6 shows the icons in alphabetical order. Alarm emergency icon 602 is shown whenever the system is significantly malfunctioning, such as when there is a major air leak, or when there is software or microprocessor failure.

Alarm sound off icon 604 is shown when the user has continued to operate the cuff in an inflated state after the conclusion of the specified period for inflation.

Air leak icon 606 is shown whenever an air leak occurs, whether the leak is a major leak requiring immediate system shutdown or a minor leak that need not be addressed until after the completion of any pending surgical procedure. If the air leak has been identified as relating exclusively to one of the cuffs, the air leak icon will be shown on the side of the display relating to that cuff. Otherwise, the icon will be shown in the middle of the display.

Battery charging icon 608 is shown whenever the battery lacks sufficient power to begin a procedure. No procedure will be started without a full battery, which may require prolonged charging.

Battery icon 610 is shown whenever the system is operating on battery, rather than ac current.

Caution icon 612 is shown whenever illegal input has been received, such as when an unduly high pressure or period of time has been entered (and rejected) or when data has been entered in the wrong order. Audible feedback is also provided.

Cuff pressurized icon 614 is shown whenever a cuff is inflated when the system is not in an inflated state. Typically, this occurs after a power failure during an inflated state.

Deflated icon 618 is shown whenever a cuff is in a deflated state.

Ready icon 628 is shown whenever the system is in a ready state.

Default display icon 630 is shown whenever the system is in a default display state.

Service icon 632 is shown whenever the system requires service, whether or not it can be used to complete any pending surgical procedure.

Testing icon 636 is shown whenever the system is executing system tests as part of its startup procedure.

One of time count up 640 and time count down 638 icons is shown depending on whether the timer mode has been set to count up or count down. In time count down mode, the system displays the amount of time remaining before the appropriate cuff will be deflated. In time count up mode, the system displays the amount of time that the cuff has already been inflated.

In the preferred embodiments, the user interface is designed not only to display information concerning the current state of the surgical tourniquet in an easy to comprehend manner but also to reject illegal or inappropriate input in a manner that informs the user of the surgical tourniquet that such input has been rejected. As discussed above, the user interface will not accept a pressure above 450 millimeters of mercury or a time period initially exceeding two hours and will give audible feedback when rejecting such input. In addition, the surgical tourniquet will give audible feedback when inappropriate state changes are attempted, such as inflating from an inflated state, and when the system fails to respond correctly to proper input, such as when the system is unable to deflate due to a stuck valve. In some embodiments the audible feedback will be in the form of beeps or similar sounds, but in other embodiments, the audible feedback may be in the form of prerecorded or computer generated messages in English or other languages.

Figure 7:
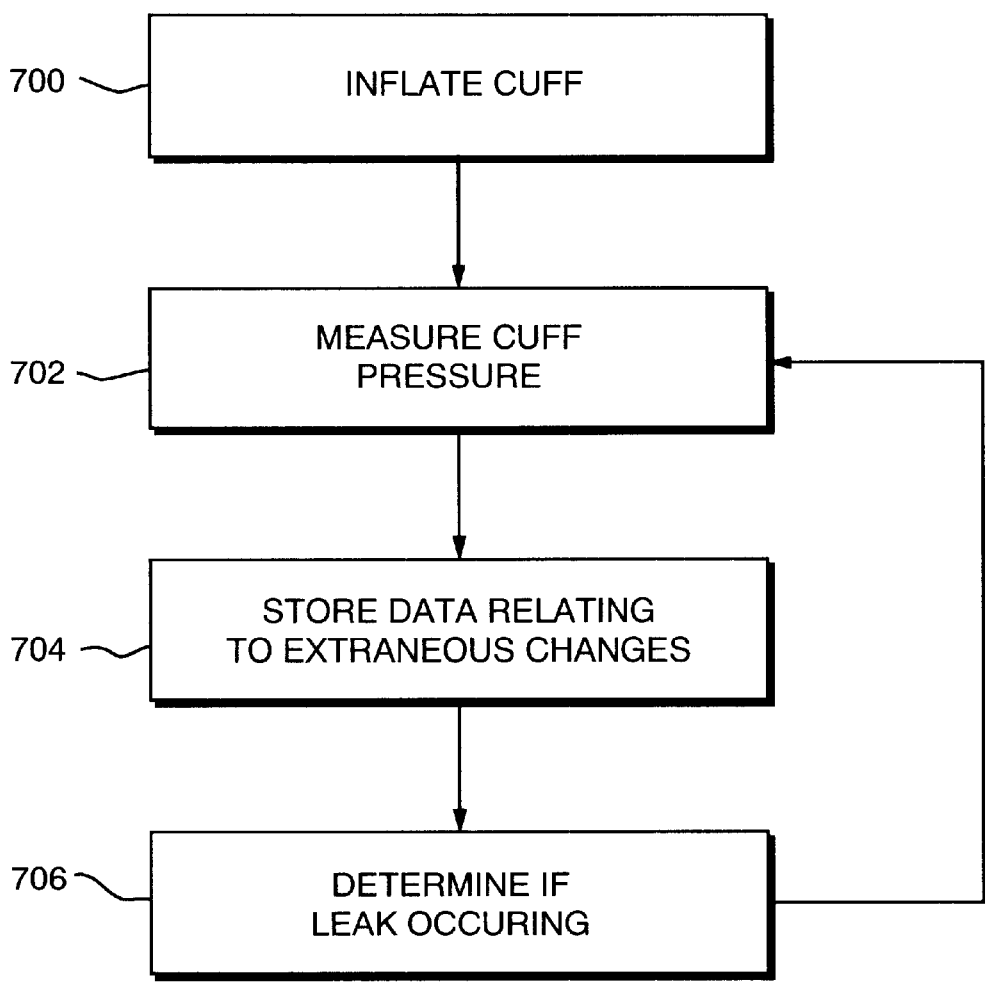
FIG. 7 is a flow diagram illustrating a method for detecting an air leak in a surgical tourniquet in accordance with a first preferred embodiment of the present invention.

Turning now to FIG. 7, a method of detecting an air leak in the surgical tourniquet is illustrated. In step 700, a cuff is inflated to an appropriate pressure. Steps 702 through 706 are then repeatedly performed until the cuff is deflated. In step 702, the controller measures the pressure within the cuff by monitoring a cuff sensor and stores each measurement in memory. The controller also stores the occurrence of any opening or closing of a valve or the operation of the pump. In step 704 the controller first establishes whether a change in pressure has been detected, second establishes whether any such change was extraneous in nature, and third stores all data relating to such change if extraneous in nature.

The controller establishes whether a change in pressure has been detected by comparing the current pressure measurement with the previous pressure measurement relating to that cuff. The controller then determines whether the change in pressure was extraneous by checking whether any valve openings or closings, or the operation of the pump, should have caused the pressure change. If not, any change is extraneous. Then, the controller stores in the memory data relating to any such extraneous changes.

In step 706, the controller determines if a leak is occurring by comparing the data relating to extraneous changes stored in all iterations of step 704 with predetermined criteria. For example, the controller might determine that a leak was occurring if the absolute or percentage decrease in pressure due to extraneous reasons from one pressure reading to the next or within a given period of time was greater than a predetermined amount or percentage. In addition, the controller might determine that a leak was occurring if more than a predetermined percentage of all or a first predetermined number of a second predetermined number of extraneous changes in pressure were decreases in pressure. The controller might also determine that a leak was occurring if the slope of the pressure within the cuff during any period in which no non-extraneous changes in pressure had occurred was not zero, or was negative, or was less than some (negative) number.

Figure 8:
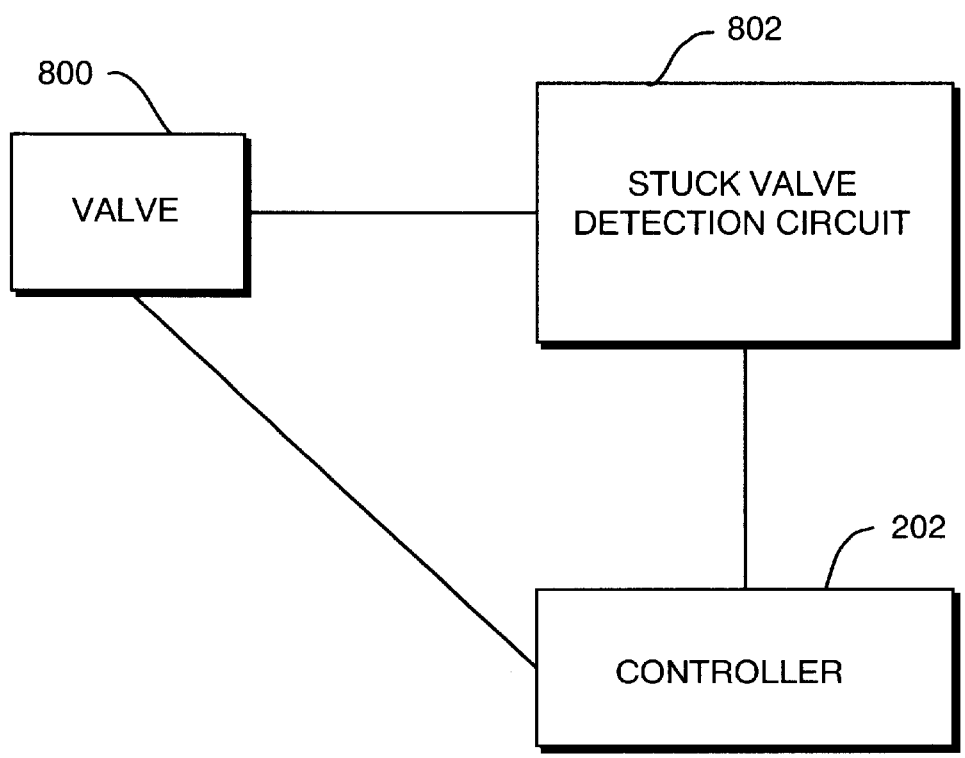
FIG. 8 is a block diagram illustrating circuitry used for detecting stuck valves in a surgical tourniquet in accordance with a first preferred embodiment of the present invention.

Referring to FIG. 8, a system for detecting a stuck valve is illustrated. A valve, which may be any of cuff valves 110A and 110B, exit valves 112A and 112B, side valves 114A and 114B, and one way valve 116, is connected both to controller 202 and to stuck valve detection circuit 802, which in turn is also connected to controller 202. In the preferred embodiments, each valve is a solenoid valve and each valve is connected to a stuck valve detection circuit, which is available from Motorola as MC33293A.

Figure 9:
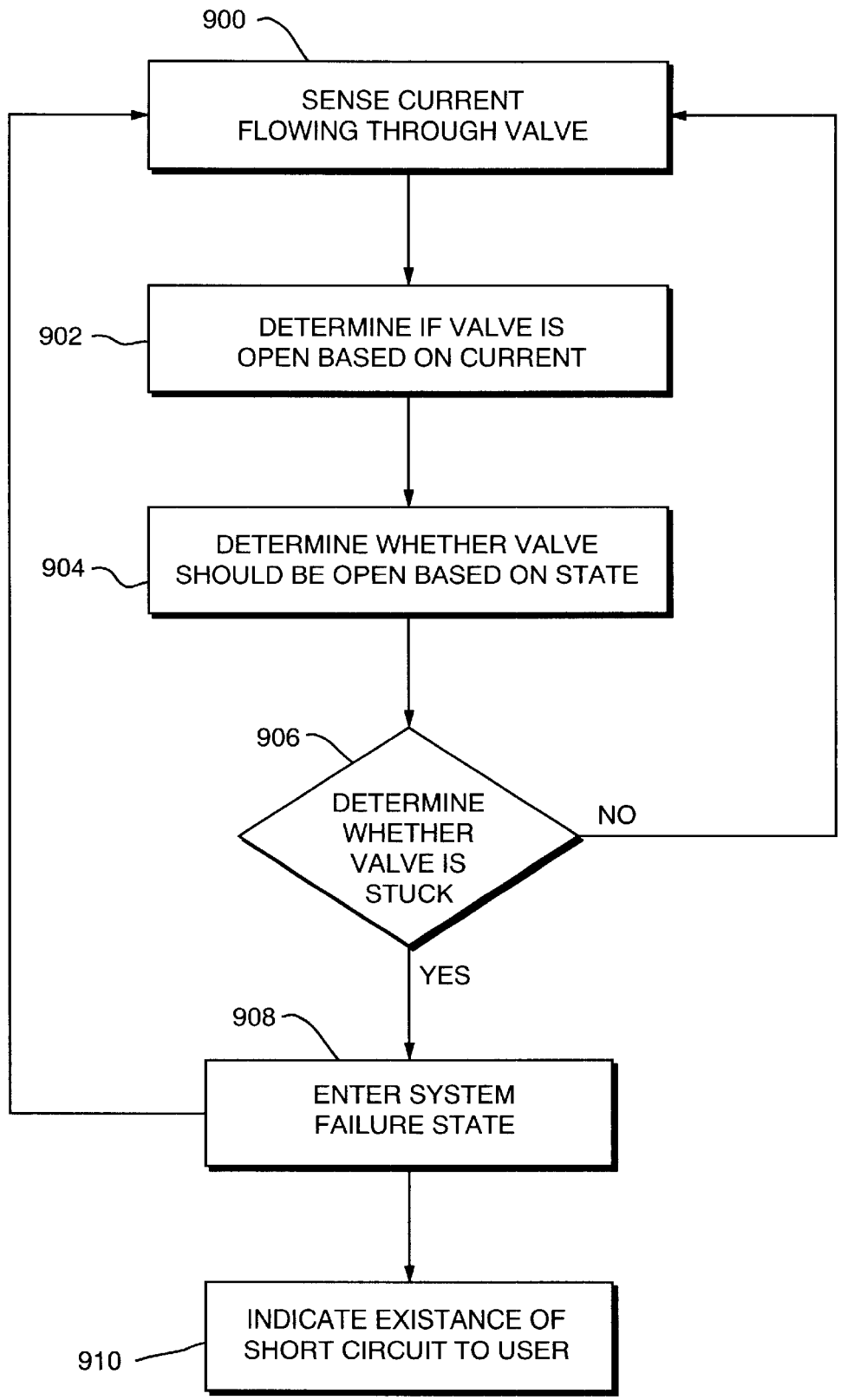
FIG. 9 is a flow diagram illustrating a method for detecting a stuck valve in a surgical tourniquet in accordance with a first preferred embodiment of the present invention.

Referring to FIG. 9, a method of detecting a stuck valve in a surgical tourniquet is illustrated. In step 900, the current flowing through the valve, if any, is detected by the stuck valve detection circuit. In step 902, the controller measures the current flowing through the circuit and determines whether the valve is open based on the amount of current flowing through the circuit. In step 904, the controller determines whether the valve should be open based on the state of the surgical tourniquet. For example, in an inflated state the exit and side valves would ordinarily be closed and the cuff valve open. In step 906, the controller compares whether the valve is open with whether the valve should be open. If the valve is open and should be open, or is closed and should be closed, the controller concludes that the valve is not stuck and returns to step 900 and continues to monitor the valve. If, on the other hand, the valve is open but should be closed, or is closed but should be open, the controller determines that the valve has failed, causes the system to enter a system failure state, and optionally indicates to the user the existence of a short circuit through visual or audible signals, or both.

Referring to FIGS. 10A through 10H, a housing 1002 containing display 204, equilibrium bladders 120A and 120B, and most of the components of the surgical tourniquet other than the cuffs, is illustrated. Taken together, FIGS. 10A (front view), 10B (side view), and 10C (rear view) illustrate that housing 1002 can be situated on a pole 1004 so that the pole runs through the center of the housing and the center of gravity of the housing is within the pole. This center of gravity provides the housing with greater stability than prior art systems, which attached externally to poles, but had centers of gravity within the housings but not within the poles. The configuration of the present invention also offers the advantage of conserving space.

Figure 10A:
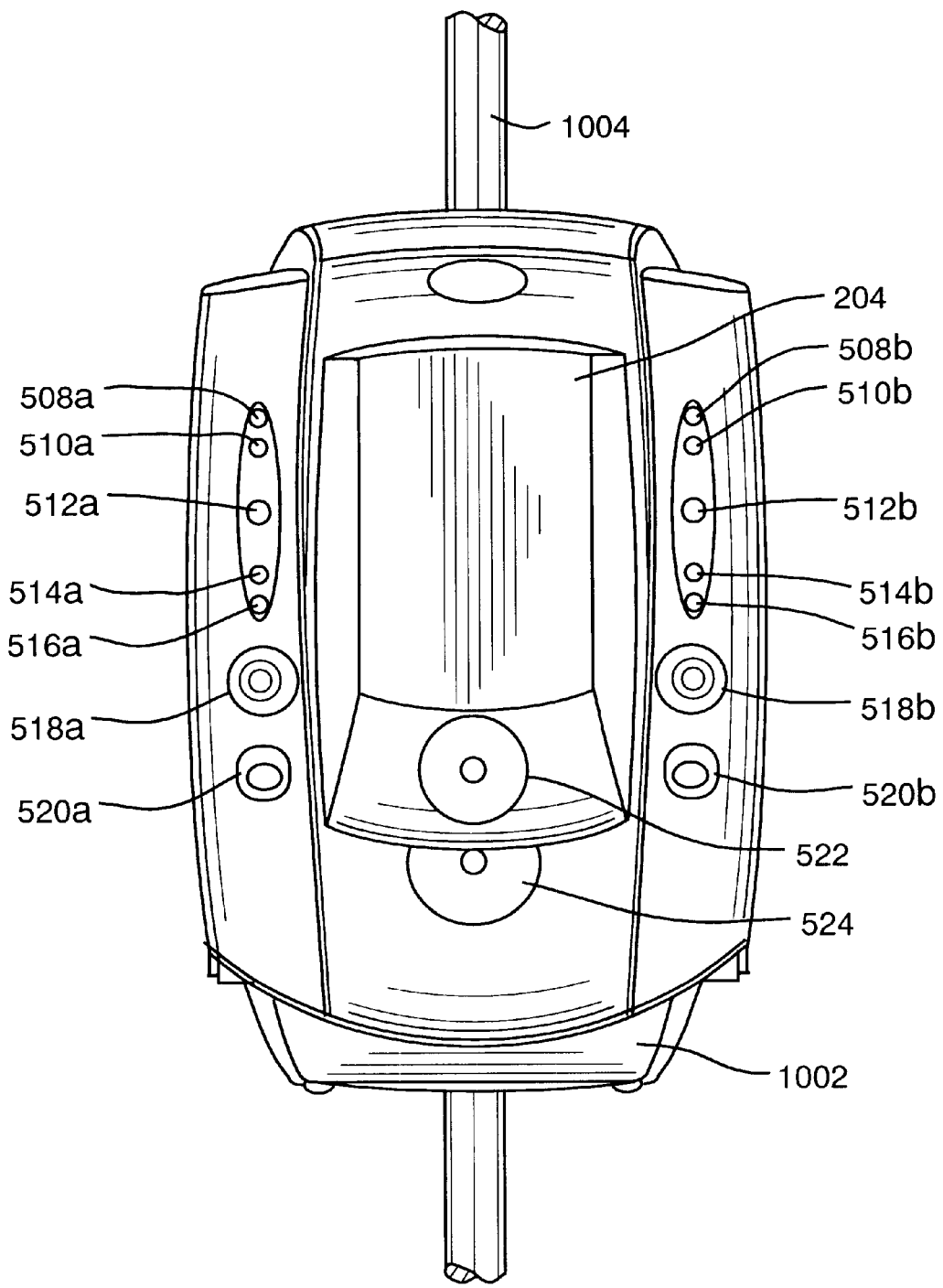
FIGS. 10A through 10H illustrate various views of a housing for portions of a surgical tourniquet in accordance with a first preferred embodiment of the present invention.
Figure 10B:
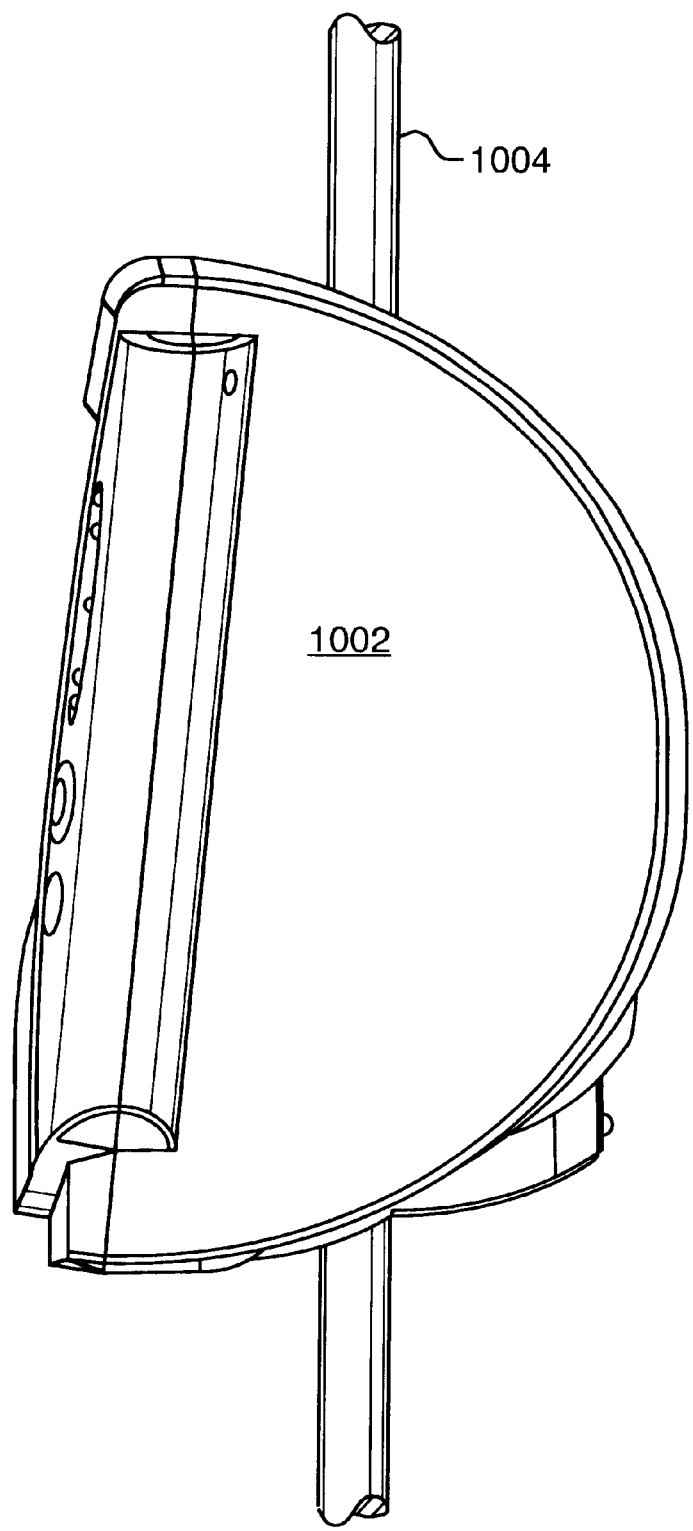
Figure 10C:
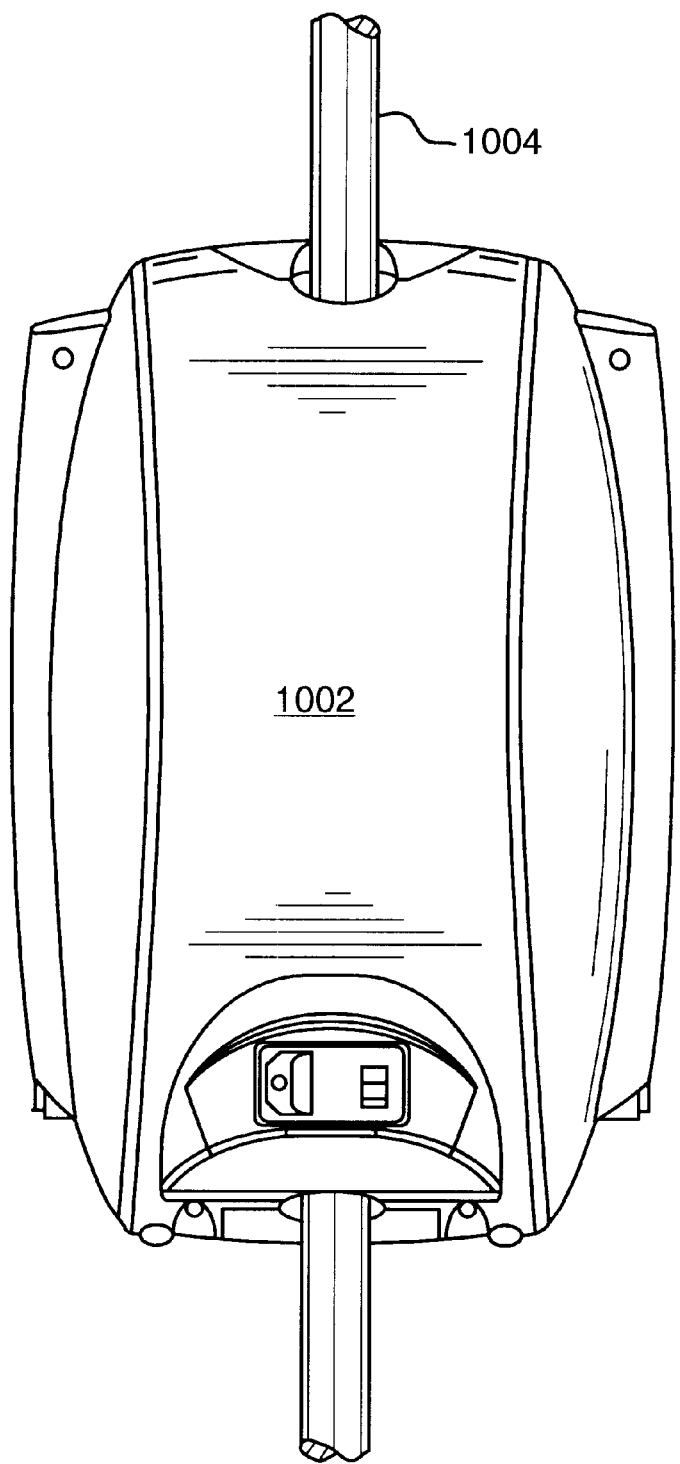
Figure 10D:
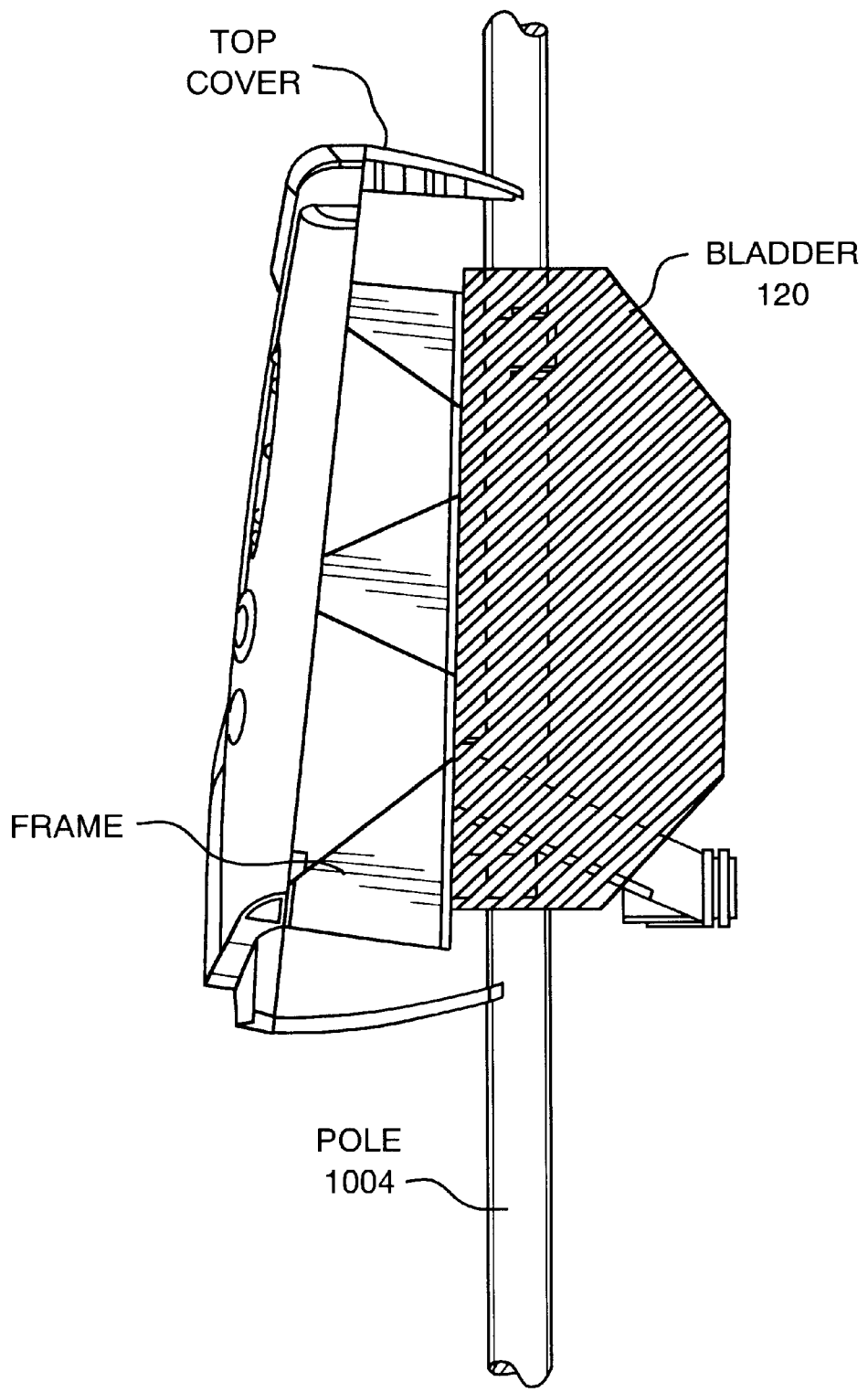
Figure 10E:
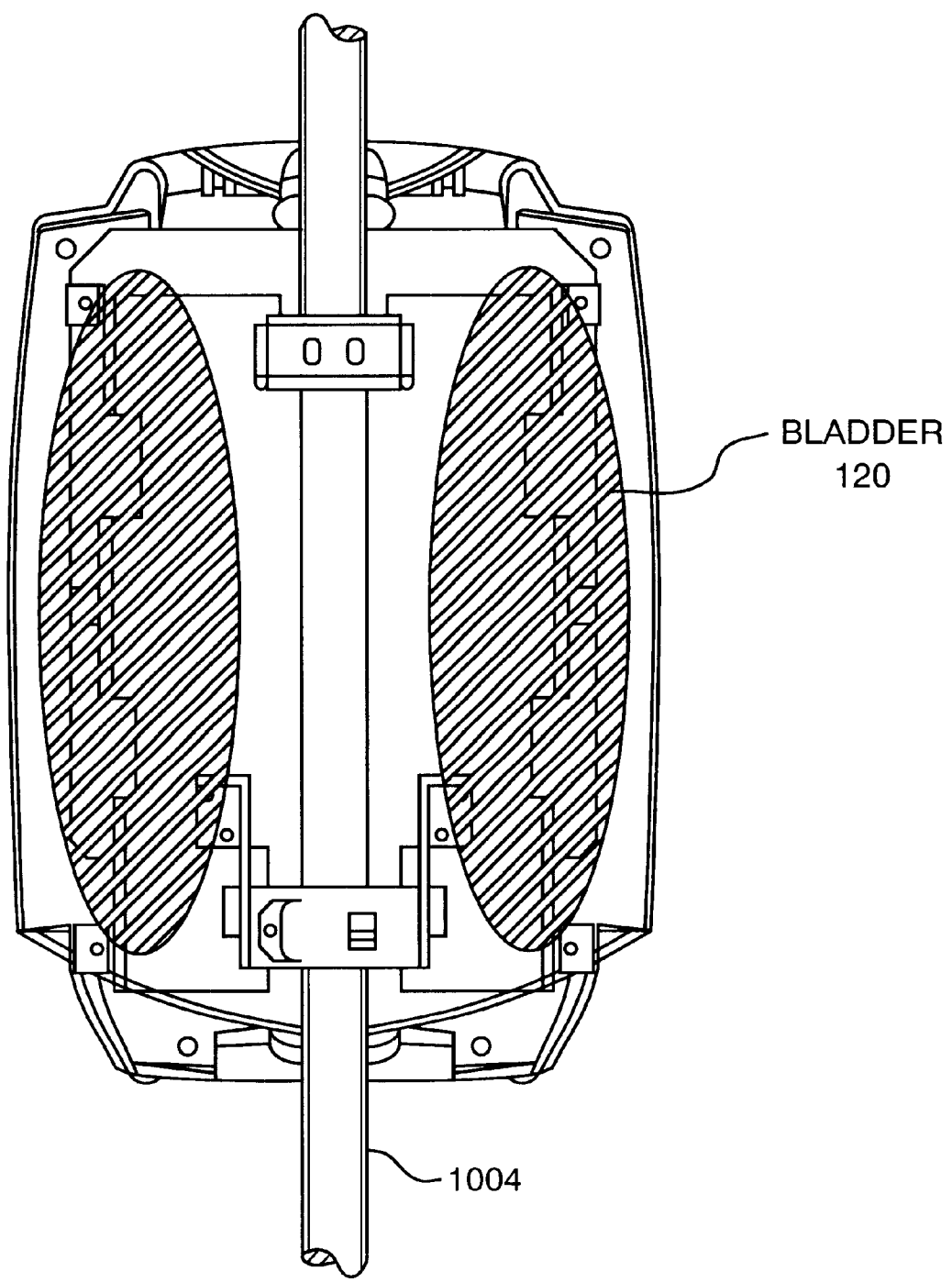
Figure 10F:
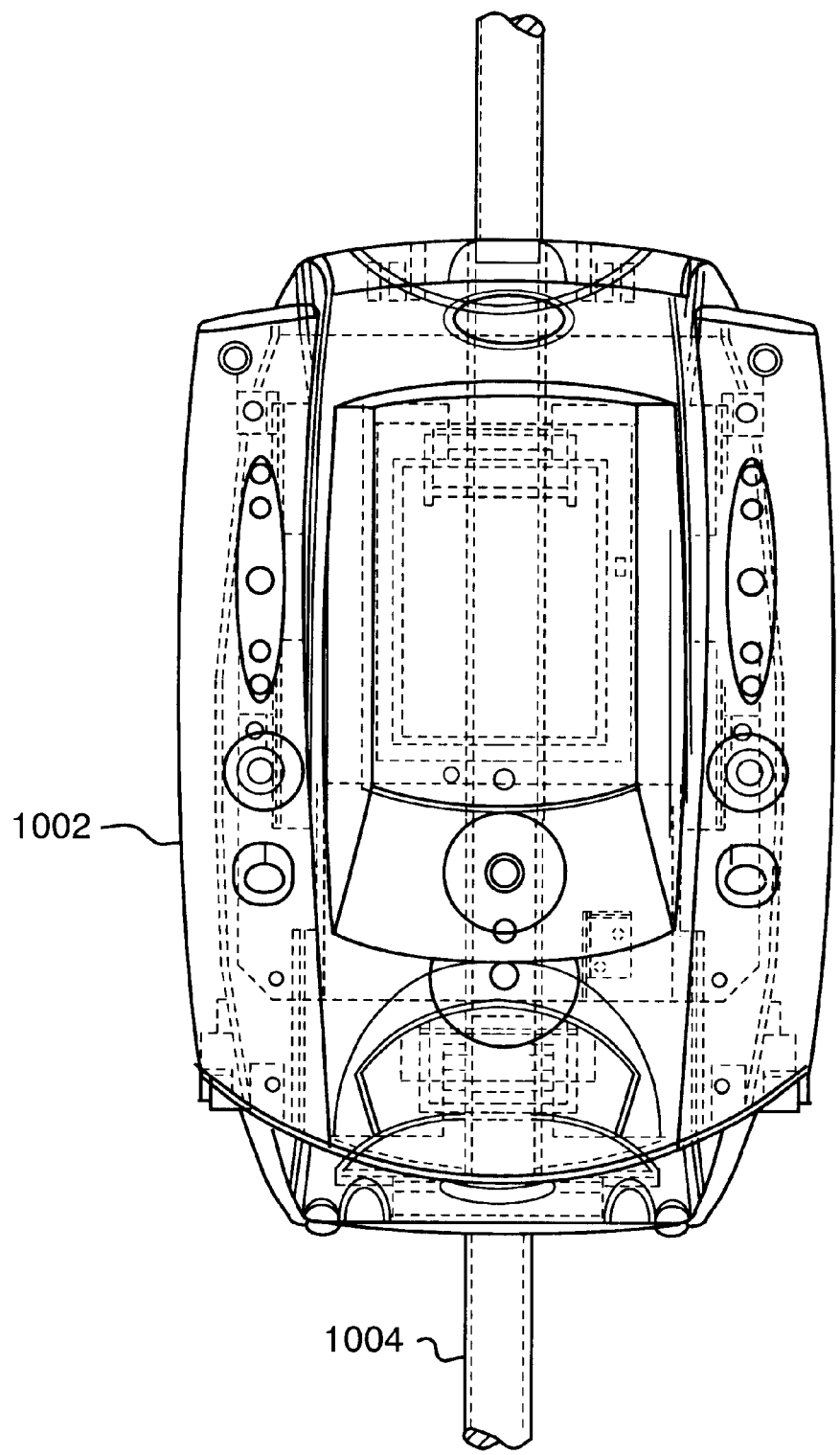
Figure 10G:
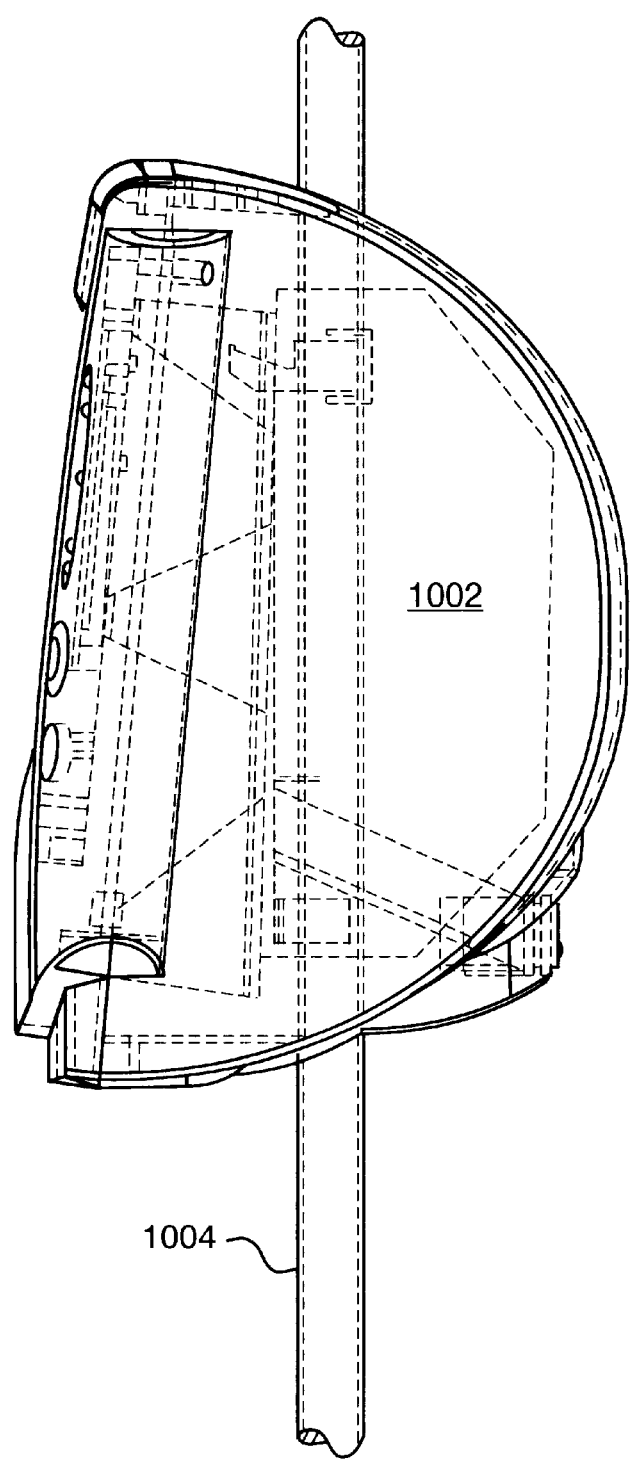
Figure 10H:
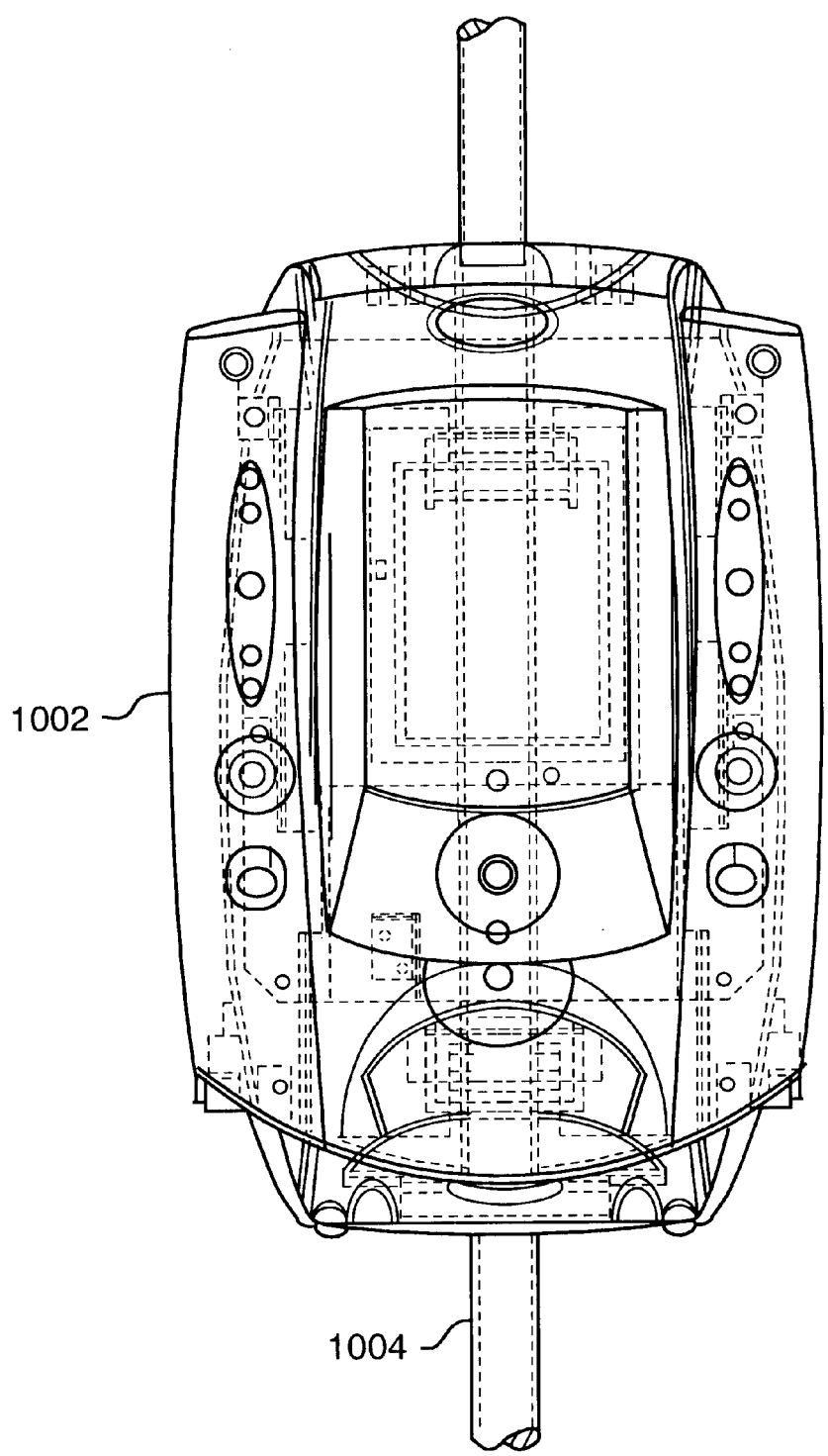

FIGS. 10D and 10E are side and front cut-away views of the housing indicating the locations of the equilibrium bladders 120. FIGS. 10F, 10G, and 10H are front, side, and rear views respectively of the housing revealing interior components.

Figure 11:
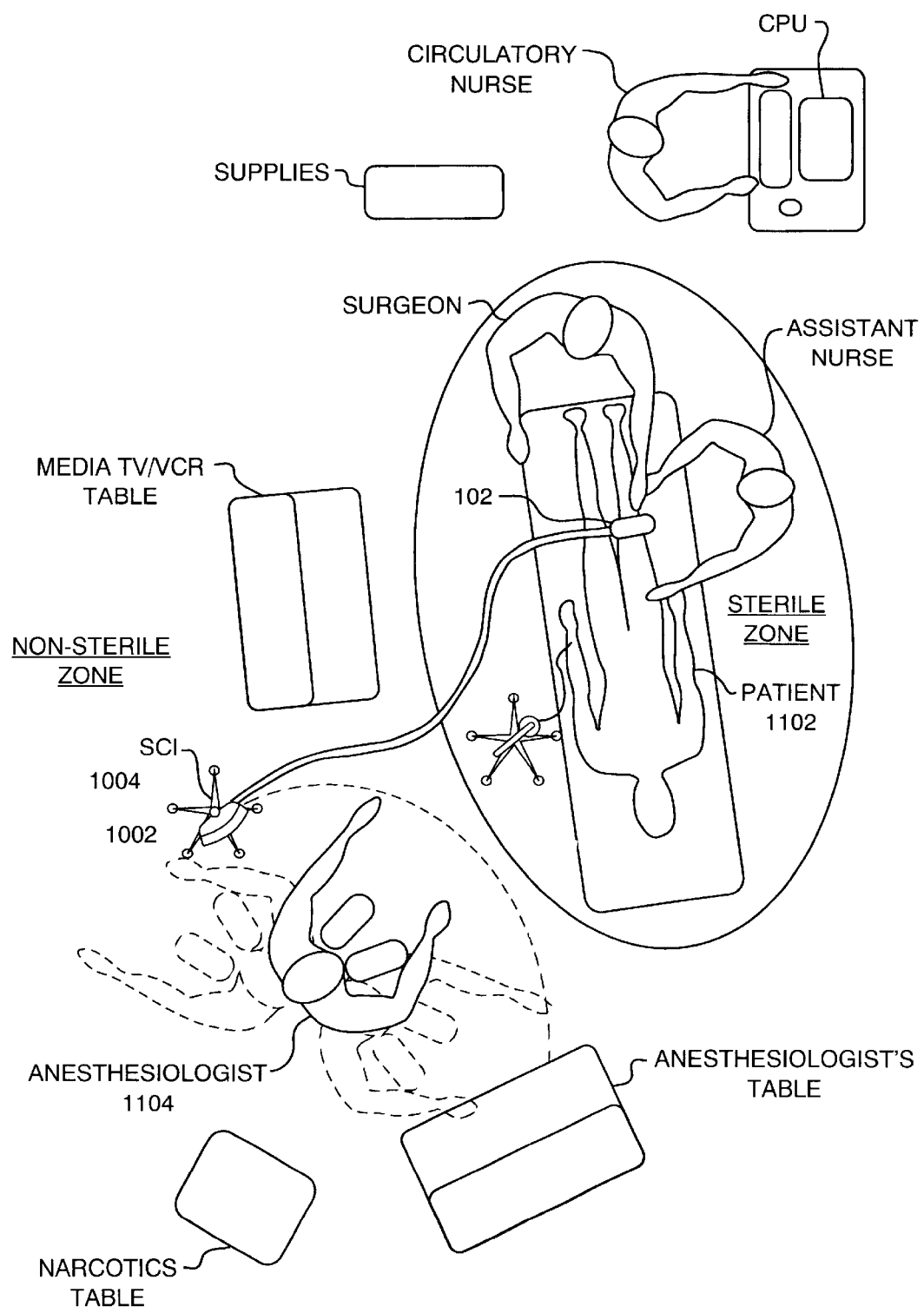
FIG. 11 is a block diagram illustrating the use of the present invention in an operating room environment in accordance with a first preferred embodiment of the present invention.

Referring now to FIG. 11, the placement of a cuff 102 around a limb of a patient 1102 is illustrated as well as the placement of the housing 1002 relative to a user 1104 of the surgical tourniquet.

The present invention may be embodied in other specific forms without departing from the spirit or essential attributes of the invention. Accordingly, reference should be made to the appended claims, rather than the foregoing specification, as indicating the scope of the invention.

What is claimed is:

1. A surgical tourniquet system, including an inflatable cuff that may be closed around a patient's limb so as to exert pressure on blood vessels within a portion of the limb, comprising;
   an inflatable cuff containing a first quantity of gas having a first internal pressure;
   an inflatable bladder containing a second quantity of gas having a second internal pressure;
   a first conduit between said inflatable cuff and said inflatable bladder;
   a first valve within said first conduit; and
   a controller connected to said first valve,
   wherein, when the pressure in said inflatable cuff is greater than that in said inflatable bladder, said controller decreases the pressure in said inflatable cuff by opening said first valve; and
   wherein, when the pressure in said inflatable cuff is less than that in said inflatable bladder, said controller increases the pressure in said inflatable cuff by opening said first valve.

2. The surgical tourniquet system of claim 1, further comprising:
   a pump connected to said controller;
   a second conduit between said pump and said inflatable bladder;
   a second valve within said second conduit and connected to said controller,
   wherein said controller increases the pressure in said inflatable bladder by opening said second valve and pumping gas from outside the surgical tourniquet system into said inflatable bladder; and
   wherein said controller decreases the pressure in said inflatable bladder by opening said second valve, thereby equalizing the pressure in said inflatable bladder with that of the atmosphere.

3. A method of controlling the pressure within a surgical tourniquet system so as selectively to occlude blood flow within a portion of a limb of a patient, comprising the steps of:
   (a) decreasing the pressure within an inflatable cuff surrounding a portion of a limb of a patient by automatically opening a first valve connected to a controller and location within a first conduit between an inflatable bladder and the inflatable cuff, when the pressure in the inflatable cuff is greater than that in the inflatable bladder, and
   (b) increasing the pressure within an inflatable cuff surrounding a portion of a limb of a patient by automatically opening said first valve connected to a controller and located within a first conduit between an inflatable bladder and the inflatable cuff, when the pressure in the inflatable cuff is less an that in the infltable bladder.

4. A surgical tourniquet system, comprising:
   an inflatable cuff containing a first quantity of gas having a first internal pressure;
   an inflatable bladder containing a second quantity of gas having a second internal pressure; and
   controller means for equalizing the first and second internal pressures.

5. A method of detecting a leak in a surgical tourniquet system, including an inflatable cuff, comprising the steps of:
   (a) first, increasing the pressure of gas within the inflatable cuff until a target pressure is reached;
   (b) thereafter, measuring the pressure of gas contained within the inflatable cuff with a pressure sensor coupled to the inflatable cuff and connected to a controller, said measurements being made repeatedly while said inflatable cuff is pressurized;
   (c) storing data relating to each pressure measurement in a memory, and
   (d) comparing each pressure measurement using predetermined criteria to determine if a leak has occurred.

6. The method of claim 5, wherein step (d) comprises determining that a leak has occurred if the percentage decrease in pressure due to an extraneous change in pressure exceeds a predetermined percentage.

7. A method in accordance with either of claim 5 or 6, further comprising the step of:
   (e) emitting an audible alarm if a leak was determined to have occurred in step (d).

8. A surgical tourniquet system, comprising:
   an inflatable cuff, containing a quantity of gas;
   a controller;
   a pressure sensor coupled to said inflatable cuff and connected to said controller, said pressure sensor measuring the pressure in said cuff; and
   a memory connected to said controller,
   where the controller determines whether a leak has occurred by continuously comparing pressure measurements from said pressure sensor to predetermined criteria.

9. A system for detecting a leak in a surgical tourniquet system, including an inflatable cuff, comprising:

(a) means for increasing the pressure of gas within the inflatable cuff until a target pressure is reached;
(b) means for repeatedly measuring the pressure of gas contained within the inflatable cuff with a pressure sensor coupled to the inflatable cuff and connected to a controller;
(c) means for storing data relating to each extraneous change in pressure in a memory; and
(d) means for continuously comparing pressure measurements from said means for repeatedly measuring the pressure of gas contained within the inflatable cuff using predetermined criteria to determine if a leak has occurred.

10. A surgical tourniquet system comprising an inflatable cuff and a controller, said inflatable cuff containing a quantity of gas, wherein said surgical tourniquet system functions in a set of states including an inflated state, a deflated state, a set state, a default display state, and an off state,
wherein an operator may define parameters identifying a desired inflatable cuff condition when surgical tourniquet system is in said set state;
wherein from an inflated state the surgical tourniquet system may enter a deflated state;
wherein from an inflated state the surgical tourniquet system may enter a set state;
wherein from an inflated state the surgical tourniquet system may enter a default display state;
wherein from an inflated state the surgical tourniquet system may enter an off state; and
wherein from said set state the surgical tourniquet system may enter an inflated state in which the quantity of gas in the inflatable cuff is varied to conform with parameters identified in said set state prior to said inflated state.

11. The surgical tourniquet system of claim 10,
wherein from a deflated state the surgical tourniquet system may reenter a previous inflated state in which the pressure exerted by the surgical tourniquet system on blood vessels in the limb of a patient is identical to the pressure previously exerted on the blood vessels before deflation of the surgical tourniquet system;
wherein from a deflated state the surgical tourniquet system may enter a set state;
wherein from a deflated state the surgical tourniquet system may enter a default display state; and
wherein from a deflated state the surgical tourniquet system may enter an off state.

12. A surgical tourniquet system comprising an inflatable cuff and a controller, said inflatable cuff containing a quantity of gas, wherein said surgical tourniquet system function in a set of states including an inflated state, a deflated state, a set state, a default display state, and an off state,
wherein an operator may define parameters identifying a desired inflatable cuff condition when surgical tourniquet system is in said set state;
wherein from an inflated state the surgical tourniquet system may directly enter a deflated state;
wherein from an inflated state the surgical tourniquet system may directly enter a set state;
wherein from an inflated state the surgical tourniquet system may directly enter a default display state; and
wherein from an inflated state the surgical tourniquet system may directly enter an off state; and
wherein from said set state the surgical tourniquet system may enter an inflated state in which the quantity of gas in the inflatable cuff is varied to conform with parameters identified in said set state prior to said inflated state.

13. The surgical tourniquet system of claim 12, wherein from a deflated state the surgical tourniquet system may directly reenter a previous inflated state in which the pressure exerted by the surgical tourniquet system on blood vessels in the limb of a patient is identical to the pressure previously exerted on the blood vessels before deflation of the surgical tourniquet system;
wherein from a deflated state the surgical tourniquet system may directly enter a set state;
wherein from a deflated state the surgical tourniquet system may directly enter a default display state; and
wherein from a deflated state the surgical tourniquet system may directly enter an off state.

14. A surgical tourniquet system, comprising:
an inflatable cuff;
a controller connected to said inflatable cuff; and
a display connected to said controller;
wherein a user controls the surgical tourniquet system by means of a graphical user interface displayed on said display;
wherein the graphical user interface comprises a plurality of icons.

15. The surgical tourniquet system of claim 14, wherein the plurality of icons comprises an air leak icon displayed to indicate a gas leak in the surgical tourniquet system; and
wherein the air leak icon includes a representation of a broken geometric shape and a representation of a gas cloud.

16. The surgical tourniquet system of claim 14, wherein the plurality of icons comprises a cuff pressurized icon displayed to indicate that said cuff is currently pressurized; and
wherein the cuff pressurized icon includes a representation of a geometric shape and a plurality of representations of arrows.

17. The surgical tourniquet system of claim 14, wherein the plurality of icons comprises a deflated icon displayed to indicate that said cuff is currently deflated; and
wherein the deflated icon includes a representation of a pinched broken geometric shape and a representation of a gas cloud.

18. The surgical tourniquet system of claim 14, wherein the plurality of icons comprises an inflated icon displayed to indicate that said cuff is currently inflated; and
wherein the inflated icon includes a representation of an unbroken geometric shape.

19. The surgical tourniquet system of claim 14, wherein the plurality of icons comprises a default display icon displayed to indicate that said cuff is currently in a default display state; and
wherein the default display icon includes a representation of the letter "d".

20. The surgical tourniquet system of claim 14, wherein the plurality of icons comprises a time count down icon displayed when the cuff is in an inflated state to indicate the approximate amount of time during which said cuff is to remain pressurized;

wherein the time count down icon includes a representation of at least one hand of a clock and a representation of an outline of a face of a clock;

wherein a first portion of the representation of the outline of the face of the clock is a solid line;

wherein a second portion of the representation of the outline of the face of the clock is a broken line; and wherein the length of the first portion of the representation of the outline of the face of the clock is related to the amount of time remaining during which said inflatable cuff is to remain pressurized.

21. The surgical tourniquet system of claim 14, wherein the plurality of icons comprises a time count up icon displayed when the cuff is in an inflated state to indicate the approximate amount of time during which said cuff has been in an inflated state;

wherein the time count up icon includes a representation of at least one hand of a clock and a representation of an outline of a face of a clock;

wherein a first portion of the representation of the outline of the face of the clock is a solid line;

wherein a second portion of the representation of the outline of the face of the clock is a broken line; and wherein the length of the first portion of the representation of the outline of the face of the clock is related to the amount of time during which said inflatable cuff has been in an inflated state.

\* \* \* \* \*